United States Patent
Ackley, Jr. et al.

(10) Patent No.: US 7,456,946 B2
(45) Date of Patent: Nov. 25, 2008

(54) LASER SYSTEM FOR PELLET-SHAPED ARTICLES

(75) Inventors: E. Michael Ackley, Jr., Mannington, NJ (US); Daniel J. Palmer, Quakertown, NJ (US)

(73) Assignee: Ackley Machine Corporation, Moorestown, NJ (US)

( * ) Notice: Subject to any disclaimer, the term of this patent is extended or adjusted under 35 U.S.C. 154(b) by 0 days.

(21) Appl. No.: 11/496,488

(22) Filed: Aug. 1, 2006

(65) Prior Publication Data

US 2006/0268264 A1 Nov. 30, 2006

Related U.S. Application Data

(62) Division of application No. 10/705,821, filed on Nov. 13, 2003, now Pat. No. 7,102,741.

(60) Provisional application No. 60/493,769, filed on Aug. 11, 2003, provisional application No. 60/425,738, filed on Nov. 13, 2002.

(51) Int. Cl.
  *G01N 21/00* (2006.01)
  *B23K 26/38* (2006.01)

(52) U.S. Cl. ............ 356/237.1; 219/121.7; 219/121.71; 250/223 R

(58) Field of Classification Search ... 356/237.1–237.6, 356/428–431; 250/559.29; 219/121.83, 219/121.7, 121.67, 559.29; 372/13, 26, 10, 372/12

See application file for complete search history.

(56) References Cited

U.S. PATENT DOCUMENTS

| | | | |
|---|---|---|---|
| 1,334,822 | A | 3/1920 | Varble |
| 2,613,594 | A | 10/1952 | Emerson |
| 3,052,552 | A | 9/1962 | Koerner et al. |
| 3,084,781 | A | 4/1963 | Merrill |
| 3,215,536 | A | 11/1965 | Simeone et al. |

(Continued)

FOREIGN PATENT DOCUMENTS

DE  3836142 A1  6/1999

(Continued)

OTHER PUBLICATIONS

Cognex Website (9 pages) with copyright notice of 2001.

*Primary Examiner*—Hoa Q Pham
(74) *Attorney, Agent, or Firm*—Nixon & Vanderhye P.C.

(57) ABSTRACT

A pellet-shaped article inspection unit is structured for use with a conveyer mechanism having a plurality of carrier bars, each carrier bar being structured to convey a plurality of pellet-shaped articles along a predetermined path. The article inspection unit includes a first camera unit positioned adjacent a first side of the conveyer mechanism. The first camera unit is configured to sense a first predetermined characteristic, e.g., laser holes, of the plurality of pellet-shaped articles. A removal mechanism, downstream from the first camera unit, is structured to remove or maintain at least a selected one of the plurality of pellet-shaped articles from at least a selected one of the plurality of carrier bars depending on whether the first predetermined characteristic is sensed by the first camera unit. A laser unit may be provided to create unique holes in the pellet-shaped articles, e.g., those by a larger exposed surface to improve time-release characteristics of the pellet-shaped articles.

39 Claims, 22 Drawing Sheets

U.S. PATENT DOCUMENTS

| | | |
|---|---|---|
| 3,335,658 A | 8/1967 | Uschmann |
| 3,735,699 A | 5/1973 | Koelschbach |
| 3,884,143 A | 5/1975 | Ackley |
| 3,889,591 A | 6/1975 | Noguchi |
| 4,082,188 A | 4/1978 | Grimmell et al. |
| 4,235,579 A | 11/1980 | Kurz et al. |
| 4,371,081 A | 2/1983 | Satake |
| 4,397,871 A | 8/1983 | Meyer et al. |
| 4,444,470 A * | 4/1984 | Ioka et al. .................. 359/312 |
| 4,446,481 A | 5/1984 | Edamatsu et al. |
| 4,519,310 A | 5/1985 | Shimizu et al. |
| 4,528,904 A | 7/1985 | Ackley |
| 4,578,273 A | 3/1986 | Krubert |
| 4,619,196 A | 10/1986 | Matsuoka |
| 4,630,736 A | 12/1986 | Maughan et al. |
| 4,632,028 A | 12/1986 | Ackley |
| 4,648,053 A | 3/1987 | Fridge |
| 4,670,271 A | 6/1987 | Pasternak |
| 4,672,892 A | 6/1987 | Ackley |
| 4,699,274 A | 10/1987 | Saika |
| 4,757,382 A | 7/1988 | Kaziura et al. |
| 4,776,466 A | 10/1988 | Yoshida |
| 4,830,194 A | 5/1989 | Kajiura et al. |
| 4,839,497 A * | 6/1989 | Sankar et al. .......... 219/121.71 |
| 4,843,958 A | 7/1989 | Egosi |
| 4,855,146 A | 8/1989 | Murakami et al. |
| 4,901,865 A | 2/1990 | Staples |
| 4,905,589 A | 3/1990 | Ackley |
| 4,946,046 A | 8/1990 | Affleck et al. |
| 5,019,326 A | 5/1991 | Yaginuma et al. |
| 5,058,175 A | 10/1991 | Aso |
| 5,085,510 A | 2/1992 | Mitchell |
| 5,135,114 A | 8/1992 | Satake et al. |
| 5,147,047 A | 9/1992 | Ahmed et al. |
| 5,148,923 A | 9/1992 | Fraenkel et al. |
| 5,165,340 A | 11/1992 | Karlyn et al. |
| 5,186,942 A | 2/1993 | Deters et al. |
| 5,220,400 A | 6/1993 | Anderson et al. |
| 5,237,621 A | 8/1993 | Cox et al. |
| 5,305,392 A | 4/1994 | Longest, Jr. et al. |
| 5,339,964 A | 8/1994 | Gray et al. |
| 5,351,117 A | 9/1994 | Stewart et al. |
| 5,376,388 A | 12/1994 | Meyers |
| 5,376,771 A | 12/1994 | Roy |
| 5,398,818 A | 3/1995 | McGarvey |
| 5,419,438 A | 5/1995 | Squyres et al. |
| 5,423,252 A | 6/1995 | Yamamoto et al. |
| 5,429,045 A | 7/1995 | Karlyn et al. |
| 5,433,146 A | 7/1995 | Ackley |
| 5,443,164 A | 8/1995 | Walsh et al. |
| 5,505,775 A | 4/1996 | Kitos |
| 5,534,281 A | 7/1996 | Pappas et al. |
| 5,553,536 A | 9/1996 | Van Os |
| 5,558,231 A | 9/1996 | Weier |
| 5,602,646 A | 2/1997 | Bernardin et al. |
| 5,630,499 A | 5/1997 | Louden et al. |
| 5,638,961 A | 6/1997 | Satake et al. |
| 5,652,432 A | 7/1997 | Yaginuma |
| 5,655,453 A | 8/1997 | Ackley |
| 5,669,511 A | 9/1997 | Satake et al. |
| 5,695,043 A | 12/1997 | Maezuru et al. |
| 5,703,377 A | 12/1997 | Ainsworth et al. |
| 5,730,048 A | 3/1998 | Averill et al. |
| 5,735,402 A | 4/1998 | Pezzoli et al. |
| 5,746,323 A | 5/1998 | Dragotta |
| 5,768,996 A | 6/1998 | Ackley |
| 5,805,510 A | 9/1998 | Miyakawa et al. |
| 5,819,953 A | 10/1998 | Julius et al. |
| 5,834,047 A | 11/1998 | Ahn |
| 5,836,243 A | 11/1998 | Ackley |
| 5,878,658 A | 3/1999 | Ackley |
| 5,878,868 A | 3/1999 | Gotoh et al. |
| 5,894,801 A | 4/1999 | Ackley |
| 5,957,306 A | 9/1999 | Hoffman |
| 5,979,309 A | 11/1999 | Boyce |
| 6,097,493 A | 8/2000 | Satake et al. |
| 6,130,405 A | 10/2000 | Loringer |
| 6,267,997 B1 | 7/2001 | Ream et al. |
| 6,286,421 B1 | 9/2001 | Ackley |
| 6,314,876 B1 | 11/2001 | Ackley |
| 6,330,351 B1 | 12/2001 | Yasunaga |
| 6,353,203 B1 | 3/2002 | Hokodate et al. |
| 6,359,255 B1 * | 3/2002 | Yamamoto et al. ..... 219/121.71 |
| 6,421,159 B1 | 7/2002 | Sutter et al. |
| 6,541,732 B2 * | 4/2003 | Hirose et al. ............. 219/121.7 |
| 6,639,167 B1 | 10/2003 | Bjork |
| 6,680,459 B2 * | 1/2004 | Kanaya et al. ........... 219/121.7 |
| 6,720,567 B2 * | 4/2004 | Fordahl et al. ......... 250/559.29 |
| 2003/0035870 A1 | 2/2003 | Ackley, Jr. et al. |
| 2004/0013778 A1 | 1/2004 | Ackley, Jr. et al. |
| 2004/0091594 A1 | 5/2004 | Ackley, Jr. et al. |
| 2004/0094050 A1 | 5/2004 | Ackley, Jr. et al. |
| 2005/0075261 A1 * | 4/2005 | Baeck et al. ................ 510/302 |

FOREIGN PATENT DOCUMENTS

| | | |
|---|---|---|
| EP | 0442782 A1 | 8/1991 |
| EP | 0596328 A2 | 8/1994 |
| EP | 0919377 A1 | 6/1999 |
| FR | 002738638 A1 | 3/1997 |
| JP | 53-32759 | 3/1978 |
| JP | 61-10457 | 1/1986 |
| JP | 62-138279 | 6/1987 |
| WO | WO 81/01232 | 5/1981 |
| WO | WO 91/01884 | 2/1991 |
| WO | WO 97/16075 | 5/1997 |
| WO | WO 00/74938 | 12/2000 |
| WO | WO 2004/045031 A3 | 5/2004 |

* cited by examiner

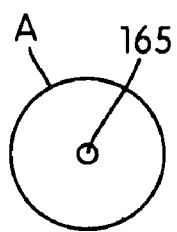 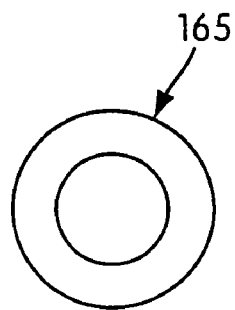
FIG. 19    FIG. 19A
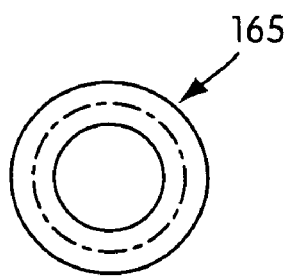 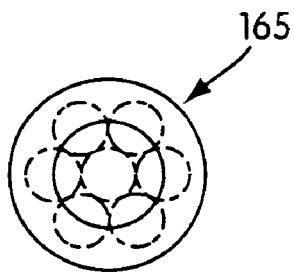 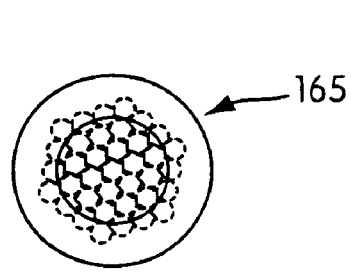
FIG. 20    FIG. 21    FIG. 22

LASER SYSTEM FOR PELLET-SHAPED ARTICLES

CROSS-REFERENCES TO RELATED APPLICATIONS

This application is a divisional of U.S. application Ser. No. 10/705,821, filed Nov. 13, 2003, now allowed, which claims the benefit of U.S. Provisional Patent Application Ser. No. 60/425,738, filed Nov. 13, 2002, and U.S. Provisional Patent Application Ser. No. 60/493,769, filed Aug. 11, 2003, the entire contents of which are herein incorporated by reference.

STATEMENT REGARDING FEDERALLY SPONSORED RESEARCH OR DEVELOPMENT (Not Applicable)

BACKGROUND OF THE INVENTION

1. Field of the Invention

The present invention also relates to processing of pellet-shaped articles, for example, pharmaceuticals such as caplets and tablets. In particular, the present invention relates to drilling holes, e.g., using a laser system, into coated pharmaceutical tablets or caplets, the drilled holes providing for mechanical time-release of medicine within the articles once ingested into the digestive track, e.g. the stomach or intestines.

The present invention also relates to inspecting the laser drilled holes against a standard and actively accepting or rejecting selected ones of the pellet-shaped articles that are properly drilled.

2. Background of the Invention

Inspection units for pellet-shaped articles are known in the art. The inspection units are typically configured to inspect and remove pellet-shaped articles from a conveyer mechanism that have been improperly processed in a previous processing operation. Previous processing operations may include marking the pellet-shaped articles with indicia, coloring the pellet-shaped articles, laser drilling holes in the pellet-shaped articles, and coating the pellet-shaped articles. These processing operations are typically completed upstream from the inspection unit such that the inspection unit may inspect if these processes have been properly completed.

For example, a variety of known devices have been developed for applying a gel coating to pellet-shaped articles. Typically, the pellet-shaped articles, e.g., tablets, capsules, caplets and pills, are coated by having one side of the pellet-shaped article coated at a time. Often, due to a processing error, one or both sides of the pellet-shaped article are not coated at all; e.g., one side of the pellet-shaped article is coated twice. As a result, the pellet-shaped article has at least one side that is not properly coated with gel. It is important for the manufacturer to carefully inspect the pellet-shaped articles for defects, such as an improperly coated side of the article, before the pellet-shaped article is distributed to the consumer so as to ensure the quality of the product and hence protect the safety of the consumer.

An example of an inspection unit is shown in U.S. Pat. No. 5,085,510 (the '510 patent). The '510 patent discloses an inspection unit for detecting laser drilled holes in tablets. As shown in FIG. 1, individual tablet carriers 6 are provided that transport individual tablets 2 in a vertical position past two sets of cameras 12. The cameras 12 are oriented horizontally and analyze opposing sides of the tablets 2 based on predetermined selection criteria. The cameras 12 signal a separation means 24 to divert preselected tablets 2. One significant limitation of the above unit is that only one tablet can be analyzed by a set of cameras at a time. As a result, more than one set of cameras must be utilized to maximize the inspection rate. Moreover, each tablet carrier 6 is only capable of transporting one tablet, which is inspected on both sides thereof. Thus, the '510 patent suffers in that the feed rate is severely limited because only one row of tablets is fed through the inspection unit.

U.S. Pat. No. 5,894,801 to Ackley, Jr., incorporated herein by reference in its entirety, describes a method and apparatus for conveying a plurality of pellet-shaped articles, such as pharmaceuticals. The conveyer conveys the pharmaceuticals past one or more article modifying devices, such as a laser that forms in the pharmaceuticals drilled or blind bore holes that act as a mechanical time-release mechanism. Lasers are known from U.S. Pat. No. 5,376,771, incorporated herein by reference in its entirety.

Known lasers create the time-release holes with a diameter in the range of about 400-800 micrometers, and a depth of about 450-500 micrometers. Depending on the medicine involved and the speed in which the medicine is to be time-released into the digestive track, the article may be provided with a plurality of holes. Typically, the holes are drilled through a coating of the article, which coating makes the article easier to swallow. The coating is encapsulates the medicine or drug until it is released through the laser hole. The coating typically will not dissolve or will dissolve more slowly than the drug or medicine. The holes are provided to allow the stomach and other fluids to penetrate the interior of the articles and thereby create a sort of pumping action to transport the medicinal portion of the article from the interior thereof into the digestive track, e.g., the stomach or intestines, etc.

The above hole dimensions, even if there are a plurality of holes, may not be suitable to allow a person's digestive fluids to penetrate the article and release the medicine in time for proper release of the medicine. Thus, the medicine may not be released along the appropriate portion of the person's digestive track, or it may not be released at all. This can result in diminished effectiveness of the medicine and dissatisfaction to the patient.

Moreover, systems such as shown in U.S. Pat. Nos. 5,433,146, 5,768,996 and 5,836,243, all to Ackley, Jr. and incorporated herein by reference in their entireties, are not suited for carrying out a coordinated series of drilling operations on a plurality of axially spaced rows of articles, because a typical drilling laser system is designed to be used with systems in which only one row of articles is provided.

Further, current inspection systems may require significant processing time to determine whether the processed articles are acceptable and to then separate acceptable articles from those that are unacceptable. For example, inspection of the drilled holes can slow down productivity and processing of the articles, especially if the inspection unit is to be integrated with other components, such as print stations, article handlers, etc. This is further complicated where the conveyer includes a plurality of axially spaced rows being simultaneously processed. The linear speed of systems with a single row of tablets makes it difficult if not impossible to reject only individual tablets. A single bad tablet or article typically causes several tablets, whether good or bad, to be rejected, thereby lowering the overall batch yield.

Accordingly, a need has developed in the art to provide one or more systems which address the concerns described above.

The present invention provides improvements over known inspection units such as the ones described above.

BRIEF SUMMARY OF THE INVENTION

One aspect of the invention relates to an improved inspection unit for inspecting and removing specified pellet-shaped articles from a conveyer mechanism that have been improperly processed.

Another aspect of the invention relates to an improved camera unit that senses pellet-shaped articles for a predetermined characteristic.

Yet another aspect of the invention relates to an improved carrier bar for transporting pellet-shaped articles along a predetermined path.

Still another aspect of the invention relates to an improved method of inspecting pellet-shaped articles.

A further aspect is to provide a system, e.g., a laser unit, to produce an improved laser drilled hole, usually in an improved pharmaceutical product.

One aspect of the invention is to provide a laser system in which a standard laser can be programmed to operate in various modes. In a first mode, for creating smaller sized holes, the laser system can provide drilled holes having a hole diameter (or an equivalent surface area if the hole is not circular) in the range of about 50 micrometers to about 1 mm, and preferably about 400-800 micrometers. In a second mode, for creating larger sized holes, the laser system can provide drilled holes having a hole diameter or surface dimension between about 1 mm and about 6 mm, and preferably in the range of about 3-6 mm. The same laser can be used in the first and the second modes. Of course, more than one small or large size hole may be provided to each article.

Another aspect is directed towards generally increasing the surface area of the drug or medicine which is exposed to the digestive fluids. The increased area can be in the form of, e.g., larger diameter drilled holes, or by etching, e.g., using a laser, cutting or removing a portion of the coating away from the medicine or drug, etc.

Another aspect is to provide a laser system for pharmaceutical articles such as caplets and tablets in which the laser system can provide laser drilled holes to a plurality of rows of articles as they are continuously conveyed along a conveyer.

One preferred embodiment of the invention is related to a pellet-shaped article inspection unit configured for use with a conveyer mechanism of the type including, e.g., a feed drum or a plurality of carrier bars. Either the feed drum is or the carrier bars are structured to convey a plurality of pellet-shaped articles along a predetermined path. The article inspection unit includes a first camera unit positioned adjacent a first side of the conveyer mechanism. The first camera unit is configured to sense a first predetermined characteristic of the plurality of pellet-shaped articles. A removal mechanism, downstream from the first camera unit, is structured to remove at least a selected one of the plurality of pellet-shaped articles from at least a selected portion of the conveyer mechanism depending on whether the first predetermined characteristic is sensed by the first camera unit.

Another preferred embodiment relates to a camera unit for sensing a plurality of pellet-shaped articles on a conveyer mechanism. The camera unit includes, e.g., a ring light having an opening therethrough, a lens extending through the opening, and a black/white or color ⅓ CCD coupled to the lens. Of course, other lighting, lenses and CCD sizes and types can be used.

Yet another preferred embodiment relates to a carrier bar for a conveyer mechanism that conveys a plurality of pellet-shaped articles along a predetermined path past an inspection unit having at least one camera unit and a removal mechanism. The carrier bar includes a plurality of pockets for receiving a plurality of pellet-shaped articles. Each of the pockets has a throughhole configured to allow (1) the at least one camera unit to view the pellet-shaped article, and (2) the removal mechanism to remove the pellet-shaped article from that pocket in the carrier bar.

Still another preferred embodiment is related to method of inspecting pellet-shaped articles structured for use with a conveyer mechanism including a plurality of carrier bars, each carrier bar structured to convey a plurality of pellet-shaped articles along a predetermined path. The method includes sensing at least one side of the plurality of pellet-shaped articles for a predetermined characteristic and removing at least a selected one of the plurality of pellet-shaped articles from at least a selected one of the plurality of carrier bars depending on whether the predetermined characteristic is sensed.

Yet another aspect is to provide an inspection unit to inspect the laser drilled holes to ensure they conform with a given standard. The inspection unit may include a reject system to actively accept articles meeting or exceeding the given standard, for example, by creating a burst of pressurized air (or a vacuum) each time an article is determined to be acceptable, to thereby force (or draw) away the article from conveyer and into an "accept" bin. Conversely, articles not conforming to the given standard are passively rejected, e.g., by allowing them to continue further along the conveyer until they are removed from the conveyer, e.g., by gravity, and collected in a "reject" bin.

Other aspects, features, and advantages of this invention will be described in or become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 19 is a plan view of an pellet-shaped article and drilled hole according to an embodiment of the present invention;

FIG. 19A is an enlarged view of the hole of FIG. 19 with the inner and outer circles indicating the tolerance range of an exemplary hole size;

FIG. 20 is a plan view of a hole drilled in accordance with an embodiment of the present invention with the inner and outer circles indicating the tolerance range of an exemplary hole size;

FIG. 21 is a plan view of a hole drilled in accordance with an embodiment of the present invention with the inner and outer circles indicating the tolerance range of an exemplary hole size;

FIG. 22 is a plan view of a hole drilled in accordance with an embodiment of the present invention with the inner and outer circles indicating the tolerance range of an exemplary hole size;

DETAILED DESCRIPTION OF THE INVENTION

Conveyor Mechanism

Figure 1:
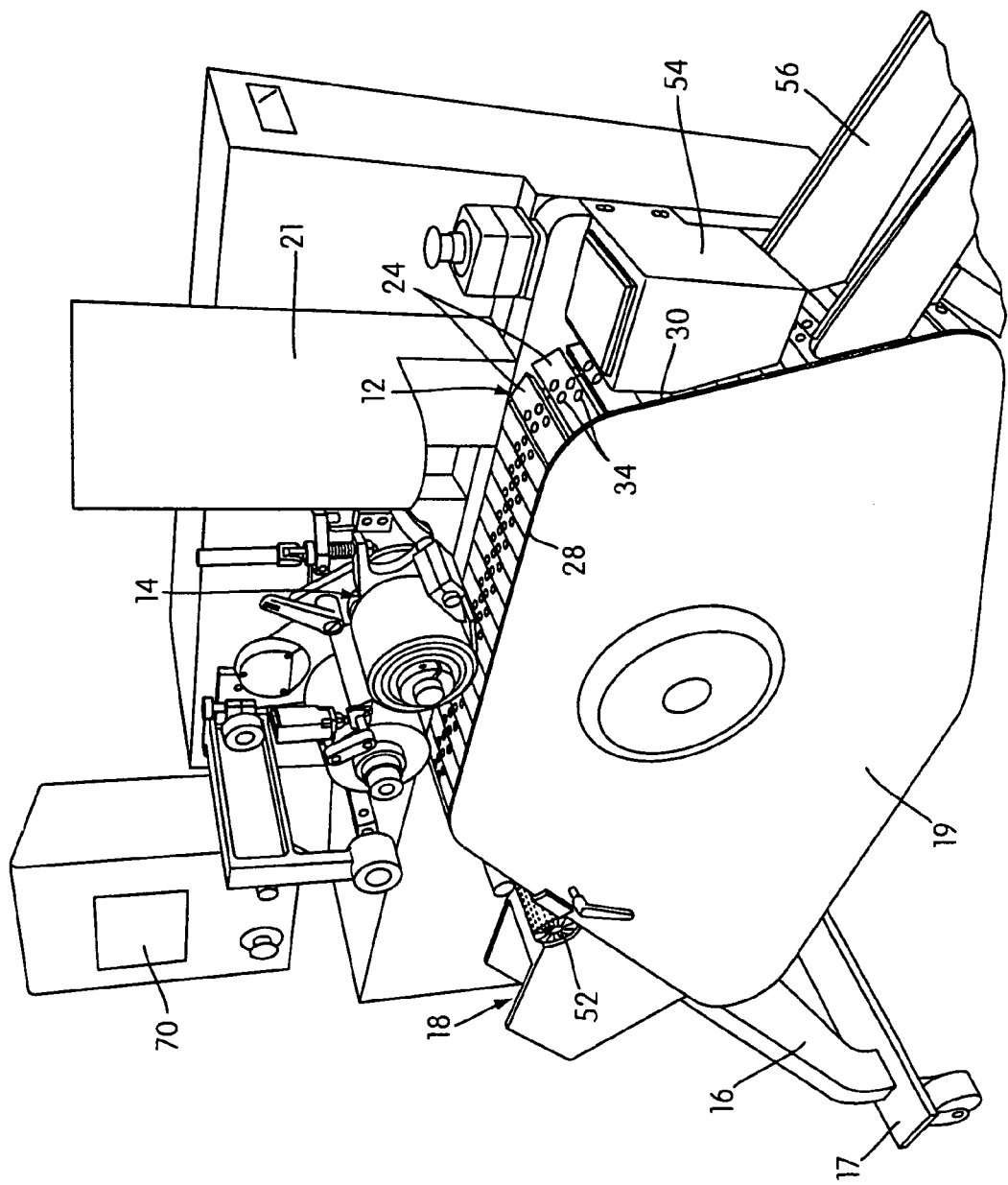
FIG. 1 is a front perspective view of one preferred embodiment of conveyer apparatus for conveying a plurality of pellet-shaped articles.
Figure 2:
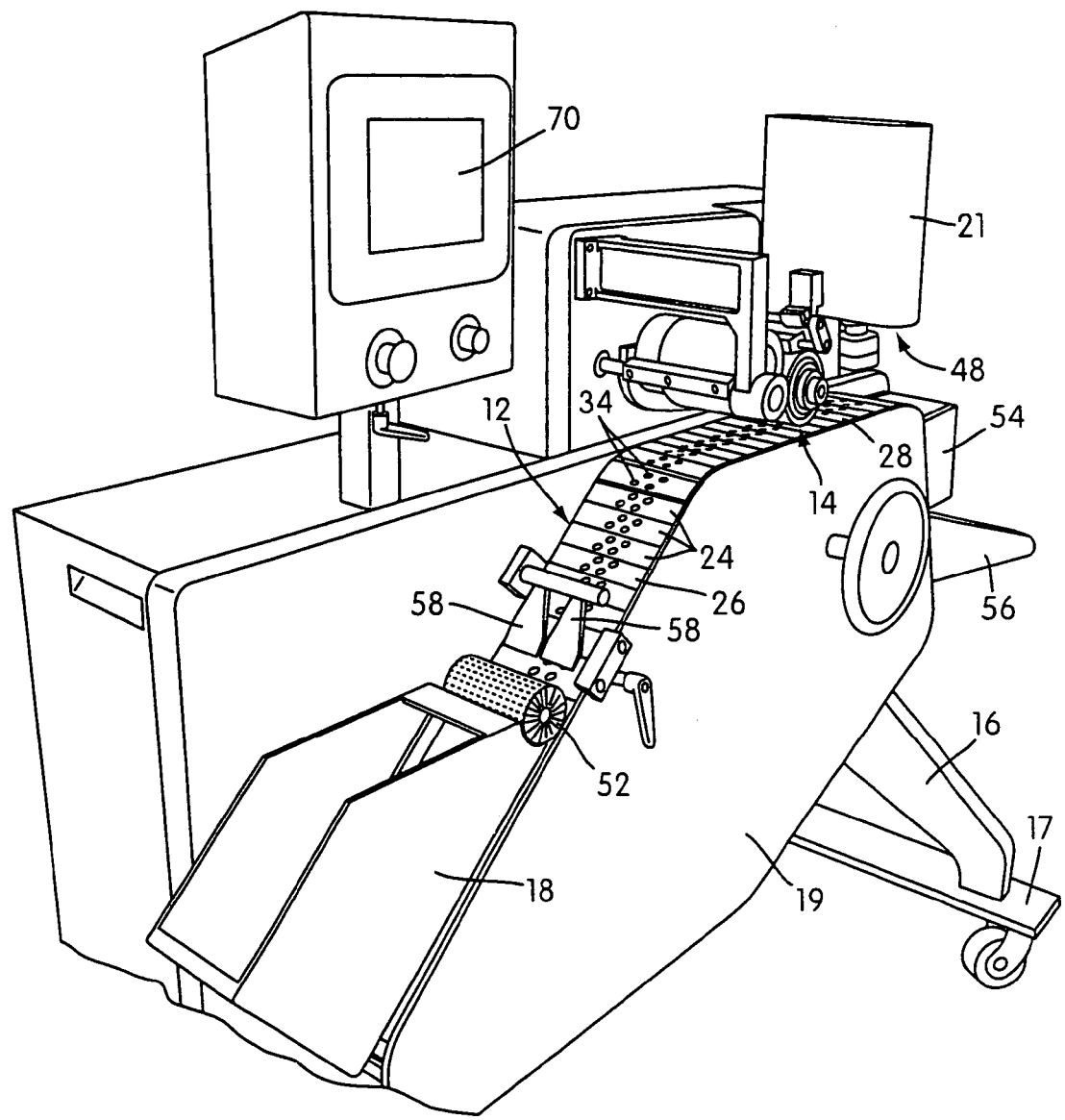
FIG. 2 is a perspective view of the conveyer apparatus shown in FIG. 1.
Figure 3:
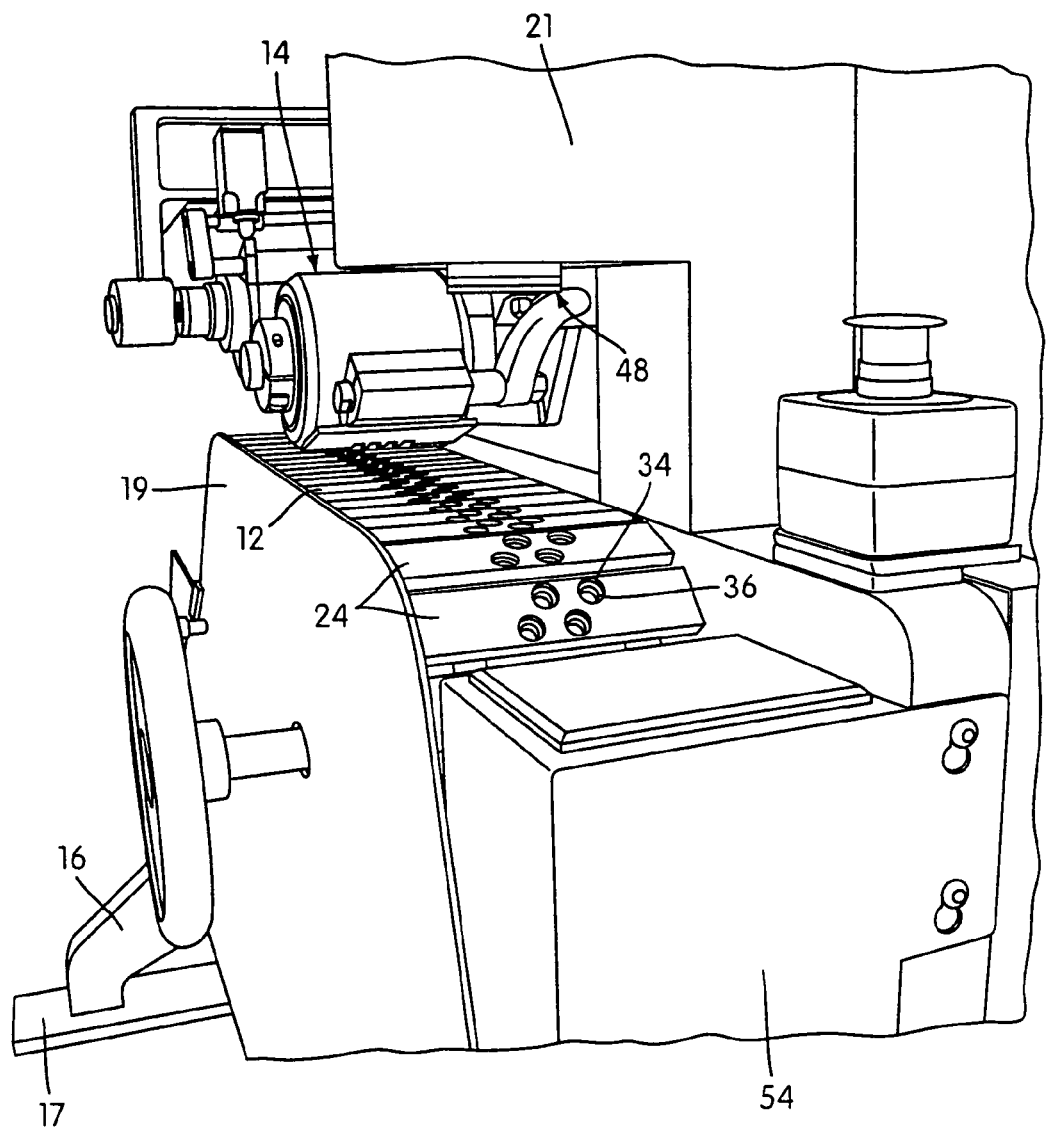
FIG. 3 is an enlarged perspective view of the conveyer apparatus shown in FIG. 1 to more clearly illustrate the carrier bars of the conveyer apparatus.

FIGS. 1-3 illustrate a conveyer mechanism 12 including a plurality of carrier bars 24 structured to convey a plurality of pellet-shaped articles along a predetermined conveyer path. The pellet-shaped articles may be in the form of capsules, caplets, pills, tablets, and other spherical, oval, cylindrical, or polygonal shapes, as well as irregularly shaped articles.

Figure 9:
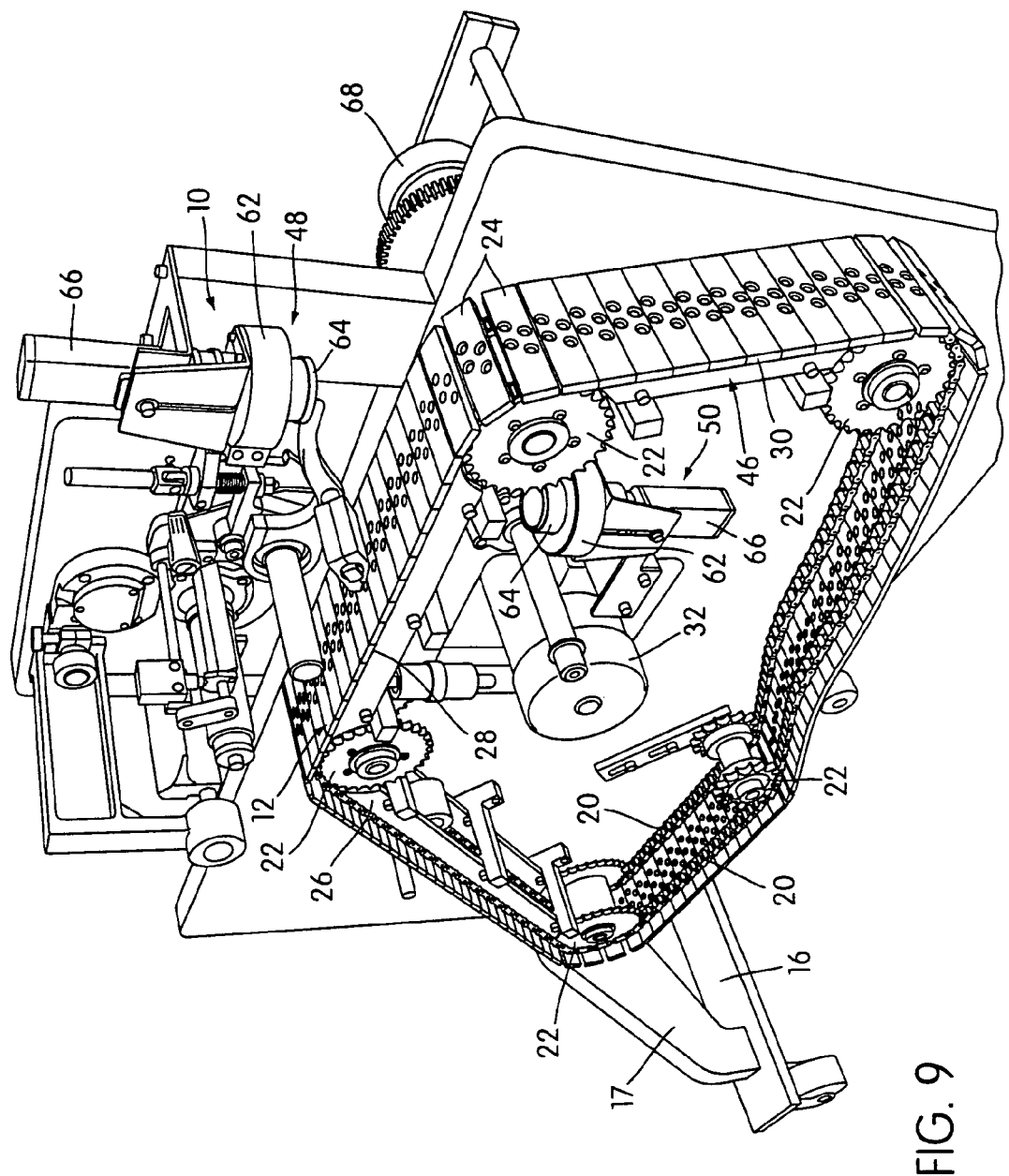
FIG. 9 is a perspective view of the conveyer apparatus shown in FIG. 1 with outer housing structures removed so as to illustrate an inspection unit.

The conveyer mechanism 12 is supported upon a frame 16 having spaced legs 17 for providing a free-standing support. The frame 16 is also structured to support a feed hopper 18, a marking apparatus 14 and first and second bins 54, 56 where pellet-shaped articles are collected, as will be further discussed. The frame 16 includes an outer housing structure 19 that encloses a drive mechanism of the conveyer mechanism 12. The frame 16 also includes an outer housing structure 21 that encloses a first camera unit 48 (FIG. 9). A display monitor 70 extends from the frame 16 and displays diagnostic information to an operator.

The feed hopper 18 is disposed over the conveyer mechanism 12 to receive a supply of pellet-shaped articles and deliver the pellet-shaped articles onto the conveyer mechanism 12, as shown in FIGS. 1 and 2. As the conveyer mechanism 12 is drawn beneath the feed hopper 18, the carrier bars 24 will become filled with pellet-shaped articles. Before proceeding from beneath the feed hopper 18, the carrier bars 24 and the pellet-shaped articles will encounter a brush 52 (FIGS. 1 and 2) that rotates, e.g., in an opposite direction than the direction of transport of the pellet-shaped articles. The brush 52 operates to return pellet-shaped articles to the feed hopper 18 that have not been received within one of a plurality of article receiving pockets 34 provided in the carrier bars 24. The brush 52 also operates to assist in seating the pellet-shaped articles within the pockets 34 of the carrier bars 24. After the carrier bars 24 pass by the brush 52, they pass under one or more blow-back members 58 (FIG. 2). Specifically, the blow-back members 58 are provided to create a burst of air to dislodge any articles seated within the pockets of the carrier bars. The ends of each blow-back member 58 may include one or more air jets or nozzles directed toward the pockets in the carrier bars. This feature can be helpful if the conveyer is running but is not desirable to allow articles in the hopper to be transported about the conveyer, e.g., when performing diagnostic tests or cleaning the conveyer.

Figure 4:
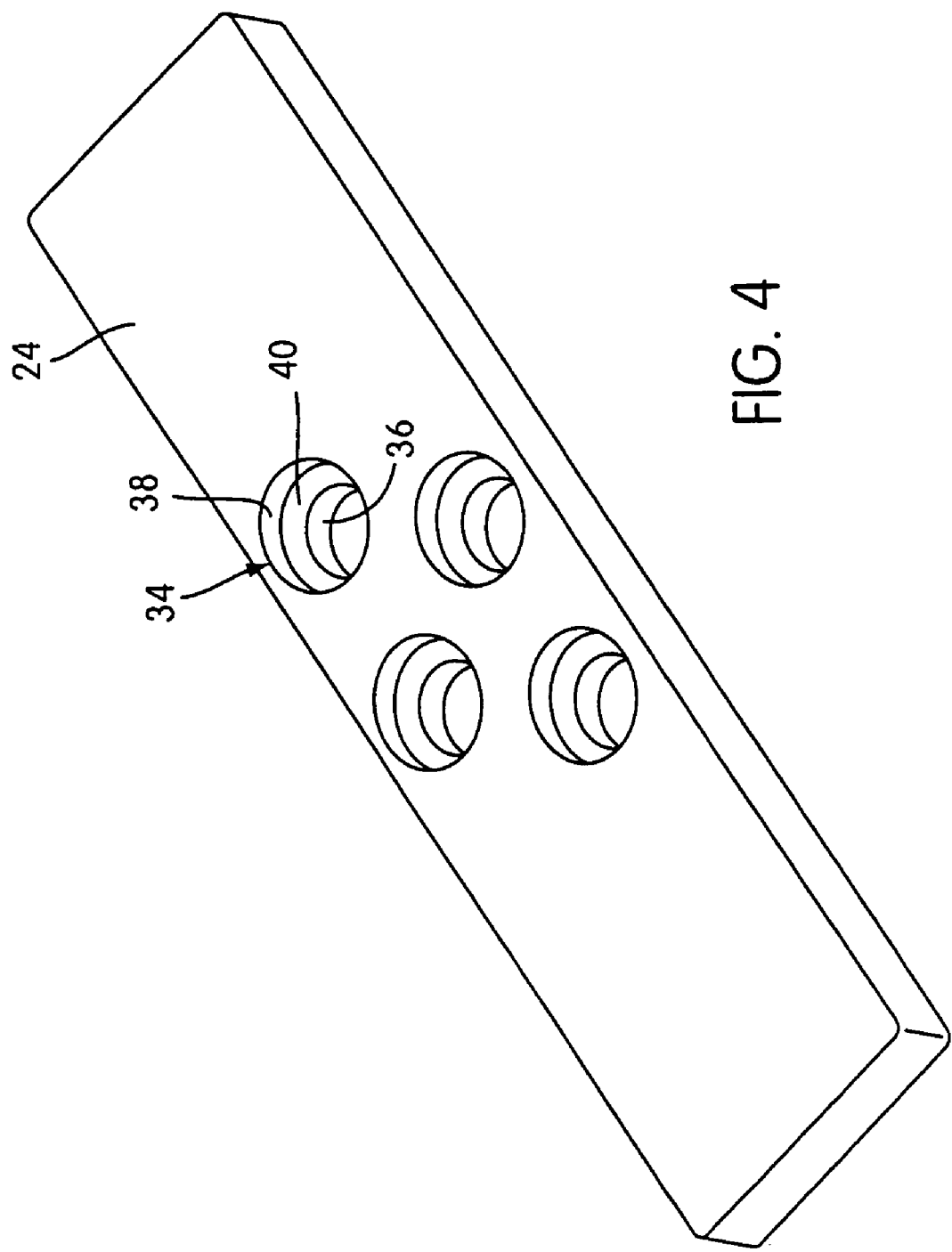
FIG. 4 is an enlarged perspective view of a carrier bar of the conveyer apparatus.
Figure 5:
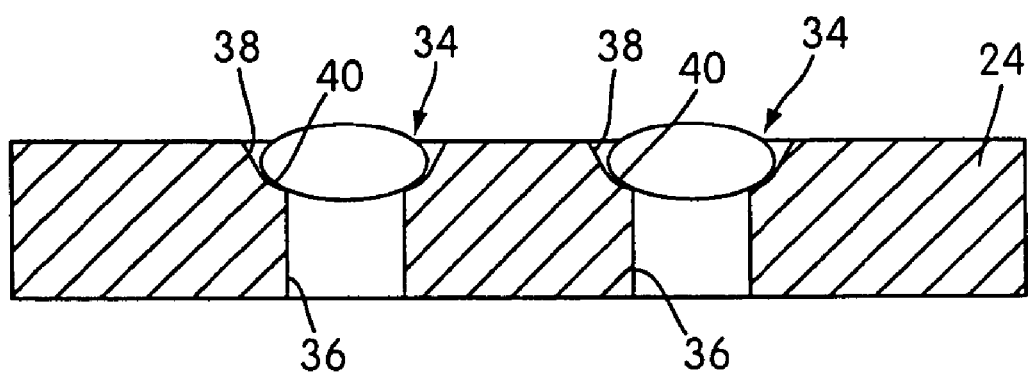
FIG. 5 is a cross-sectional view through a carrier bar to more clearly illustrate the article receiving pockets thereof.

As best shown in FIGS. 3-5, each of the carrier bars 24 is provided with one or more article receiving pockets 34, disposed transversely along their length. Each pocket 34 has a throughhole 36 that substantially matches the shape of the pellet-shaped article. Specifically, each pocket 34 includes an exterior wall 38 that defines a space in which the pellet-shaped article is to be received. An article-retaining flange 40 extends radially inwardly from the exterior wall, the inner peripheral surface of the flange 40 defining the throughhole 36. The flange 40 is suitably contoured so as to conform to the exterior shape of the pellet-shaped article. In the illustrated embodiment, the pellet-shaped article is a tablet. Thus, the retaining flange 40 of the pocket 34 holds the tablet-shaped article around the rim in a horizontal position, as shown in FIG. 5. As a result, the tablet-shaped articles within the pockets 34 are visible from an upper side of the carrier bar 24 and an inner side of the carrier bar 24 through the throughhole 36. The pockets 34 and flanges 40 thereof may be suitably modified to accommodate other shapes and sizes of the pellet-shaped articles, such as caplets and pills.

Figure 6:
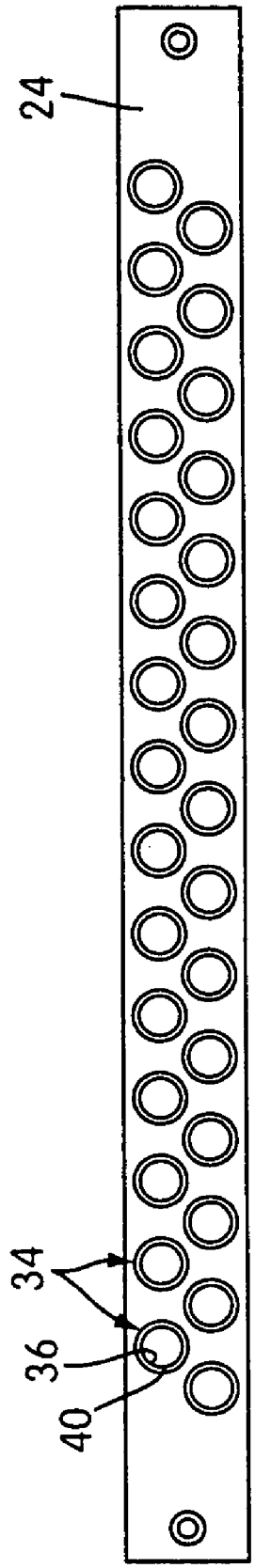
FIG. 6 is a top plan view of an alternative embodiment of the carrier bar.
Figure 7:
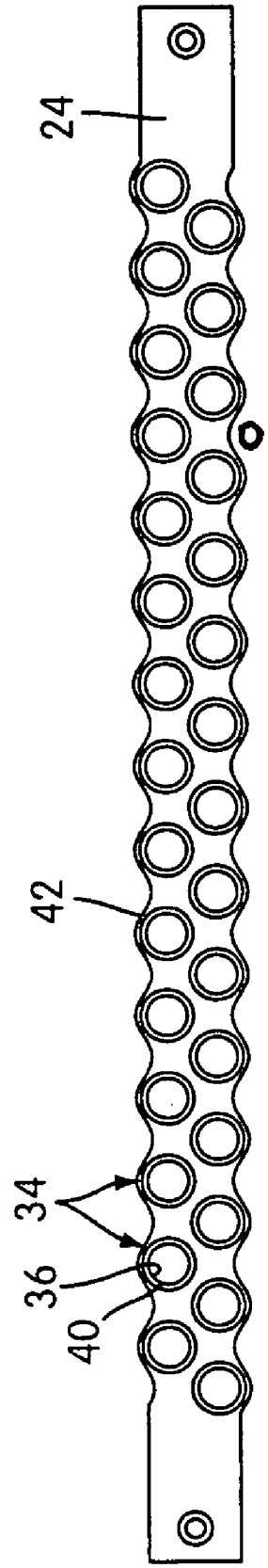
FIG. 7 is a top plan view of another alternative embodiment of the carrier bar.

The pockets 34 of the carrier bars 24 operate to receive and entrain pellet-shaped articles from the feed hopper 18 and move the pellet-shaped articles along the conveyer path. In the illustrated embodiment, each carrier bar 24 has four pockets 34. However, the carrier bars 24 may be provided with any number of pockets 24 disposed along their length. For example, the number of pockets 34 may be varied by simply varying the number of pockets 34 that are placed in line along the manufactured carrier bars 24. As shown in FIG. 6, the pockets 34 may be staggered to achieve an even greater pocket density. Further, as shown in FIG. 7, it is possible to stagger the pockets 34 along carrier bars 24 having scalloped edges 42 to further increase pocket density and conserve space. The scalloped edges 42 of the carrier bars 24 should be offset so that scalloped edges 42 of adjacent carrier bars 24 will combine to define the substantially continuous conveyer surface that is needed to effectively receive pellet-shaped articles from the feed hopper 18. Further, the pockets of one carrier bar are staggered with respect to adjacent pockets of the adjacent carrier bar.

Figure 8:
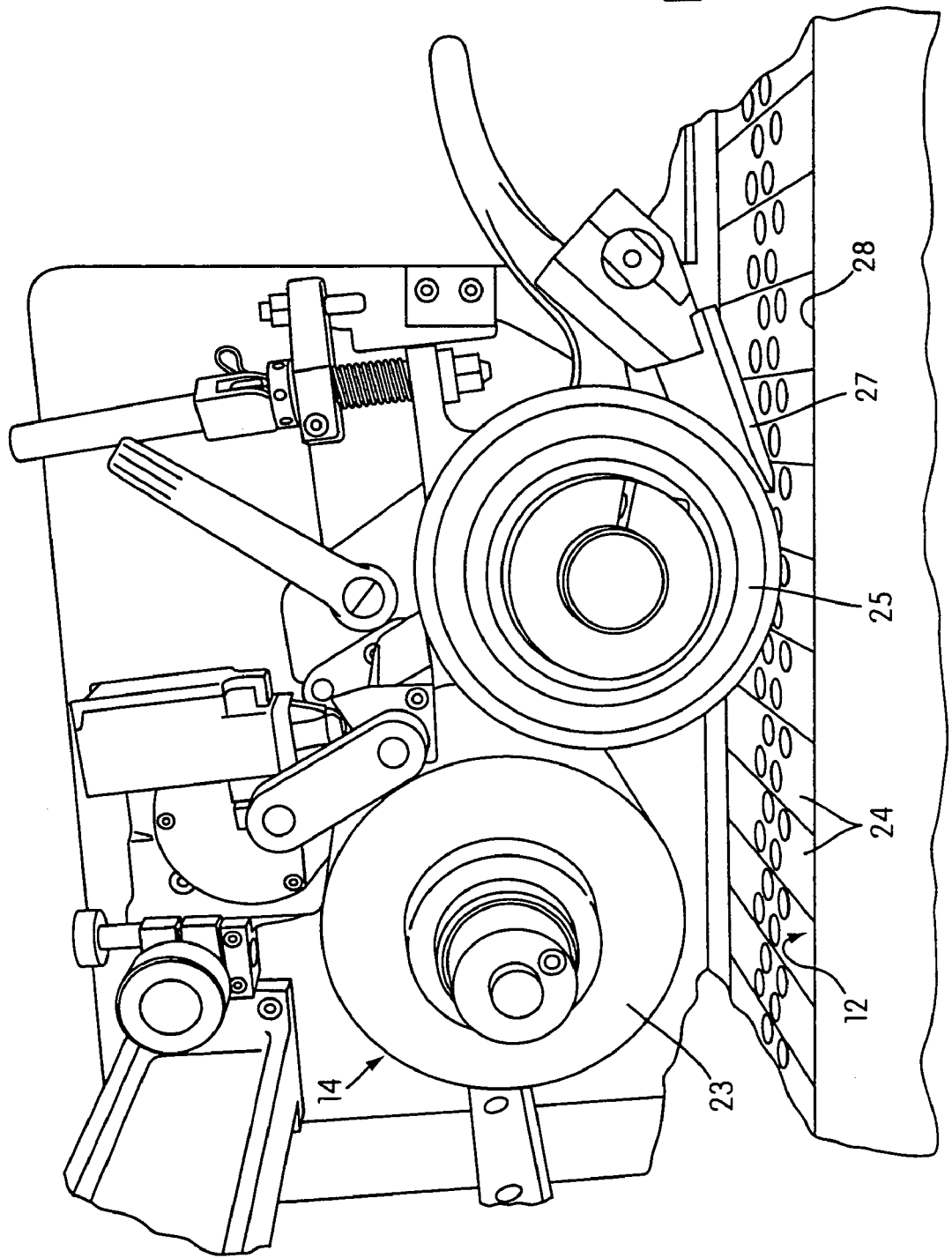
FIG. 8 is an enlarged side view of a marking apparatus.

In the illustrated embodiment, the carrier bars 24 are constructed to convey the pellet-shaped articles past a marking apparatus 14 for marking desired indicia onto the pellet-shaped articles. As shown in FIG. 8, the marking apparatus 14 includes a design roll 23 that forms the indicia to be applied to the articles, and which is disposed within an appropriate supply of ink (not shown), and a printing roll 25 which is in contact with both the design roll 23 and the pellet-shaped articles which are to receive the indicia, for transferring the ink-laden indicia from the design roll to the articles in question. A doctor blade 27 is positioned adjacent the printing roll 25 to remove excess ink from the design roll 23. Further details of the marking apparatus 14 are shown in U.S. Pat. Nos. 4,528,904 and 5,655,453 to Mr. E. Michael Ackley, Jr., which is incorporated herein by reference. It is contemplated that the marking apparatus 14 may be an ink jet.

Following the marking apparatus 14, the carrier bars 24 convey the pellet-shaped articles past the first camera unit 48. As shown in FIG. 9, the first camera unit 48 forms a part of an inspection unit 10 that inspects and removes specified pellet-shaped articles from the conveyer mechanism 12. In illustrated embodiment, the inspection unit 10 includes a first camera unit 48, a second camera unit 50, a removal mechanism 46, and a controller 60, as will be further discussed. The pellet-shaped articles that are removed are those including a defect which may have occurred in a previous processing operation.

Figure 10:
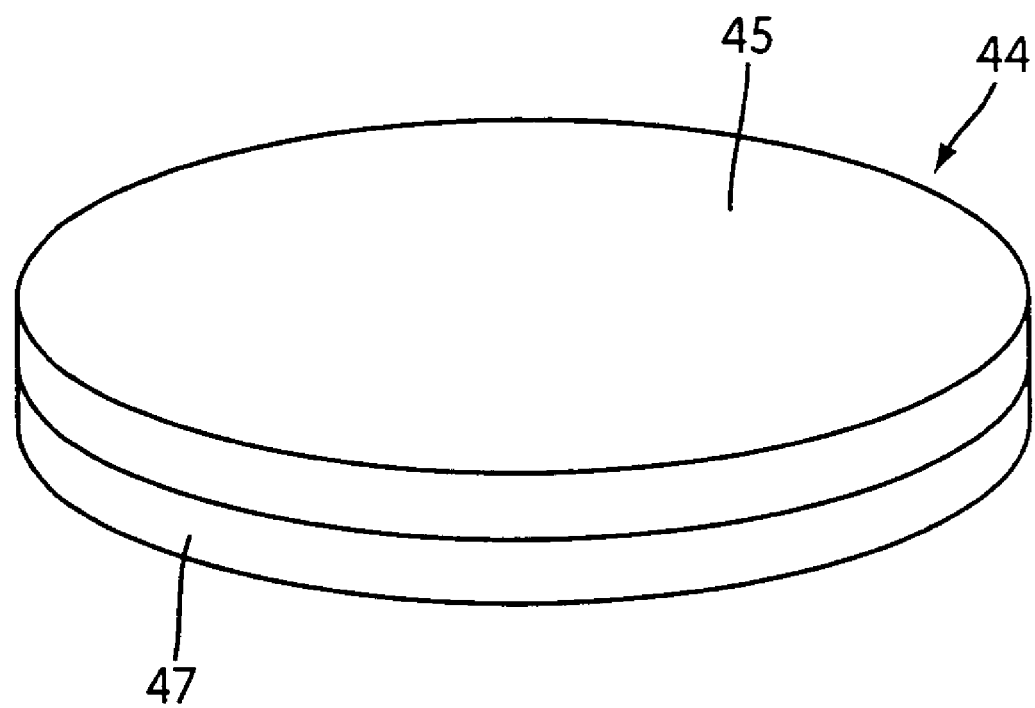
FIG. 10 is a perspective view illustrating a tablet-shaped article.

The inspection unit 10 illustrated is particularly configured to remove specified tablet-shaped articles from a conveyer mechanism 12 that have been improperly coated with gel in a previous processing operation. FIG. 10 shows a tablet 44 having a first side 45 and a second side 47. The sides 45, 47 are typically coated -with differently colored or hued gels. The coating operation is typically completed upstream from the inspection unit 10 such that the inspection unit 10 may inspect if this operation has been properly completed. The inspection unit 10 can be applied to pellet-shaped articles having the different shapes described above, as would be understood by one of ordinary skill in the art.

The inspection unit 10 of the present invention determines whether both sides 45, 47 of the tablet-shaped article 44 have been properly coated and removes specified tablet-shaped articles that have been improperly coated from the conveyer mechanism 12.

The inspection unit 10 may be configured and utilized to perform other analysis. Specifically, other processing operations may precede the inspection unit 10 such as operations that mark the pellet-shaped articles with indicia, operations that color the pellet-shaped articles, and operations that laser drill holes in the pellet-shaped articles. For example, the marking apparatus 14 precedes the inspection unit 10 for marking the pellet-shaped articles with desired indicia. The inspection unit 10 may be configured to determine whether the pellet-shaped article has been properly marked with the desired indicia and to remove specified pellet-shaped articles that have been improperly marked from the conveyer mechanism 12. See U.S. Pat. No. 5,894,801 to Ackley Machine Corporation, which is incorporated herein by reference.

Further, a variety of known apparatuses have been developed for drilling holes through coated pellet-shaped articles to provide a release path for the active ingredient. The articles may be coated with a sugar coat, a gel coat, a film coat, an enteric coat or an insoluble coat. An enteric coat will not dissolve in the stomach, but will in the intestines. Moreover, the articles may have a first coating on one end or side and a second coating on the other end or side to thereby release different medicines within the same article at different locations within the digestive track. In another alternative, the article may include two types of medicine, and the holes may be created to initially release the first medicine, and then the second medicine once all of the first medicine has been released. In still another example, the article may include two or more coating layers one on top of the other. The inspection unit 10 may be configured to determine whether the pellet-shaped article has a hole or a properly drilled hole and to remove specified pellet-shaped articles from the conveyer mechanism 12 that do not have a drilled hole or that have improper drilled holes.

In the illustrated embodiment, the inspection unit 10 forms a part of a system for marking pellet-shaped articles. Specifically, as shown in FIGS. 1-3, the marking apparatus 14 is provided that applies desired indicia to pellet-shaped articles. However, the inspection unit 10 may be provided as a separate system from the marking apparatus 14. Further, the inspection unit 10 may be configured to determine whether each pellet-shaped article is properly coated and marked with the desired indicia. Alternatively, the inspection unit 10 may be configured to only perform a single analysis, e.g., determine whether the pellet-shaped article is properly coated. In the illustrated embodiment, the inspection unit 10 is particularly configured to sense and remove specified pellet-shaped articles from a conveyer mechanism 12 that have not been coated or that have been improperly coated.

As shown in FIG. 9, the first and second camera units 48, 50 of the inspection unit 10 are provided along the conveyer path and are configured to sense a predetermined characteristic of the tablet-shaped article 44. In the illustrated embodiment, the first camera unit 48 is configured to sense whether one side of the tablet-shaped article 44 has been properly coated and the second camera unit 50 is configured to sense whether the other side of the tablet-shaped article 44 has been properly coated. Specifically, the first and second camera units 48, 50 are configured to sense for the color white (the natural color of the tablet), which indicates that a side of the tablet-shaped article 44 has not been coated or has been improperly coated. If at least one of the first and second camera units 48, 50 determines that a tablet-shaped article 44 has not been properly coated (e.g., senses the color white), then that particular tablet-shaped article 44 will be removed by the removal mechanism 46 from the conveyer mechanism 12. Likewise, if both the first and second camera units 48, 50 determine that the tablet-shaped article 44 has been properly coated (e.g., neither the first camera unit 48 nor the second camera unit 50 sense the color white), then that particular tablet-shaped article 44 is not removed by the removal mechanism 46.

Each camera unit 48, 50 is configured to sense a plurality of pockets 34 simultaneously. In the illustrated embodiment, each camera unit 48, 50 is configured to sense four pockets 34. Thus, each camera unit 48, 50 is configured to sense the number of pockets provided in each carrier bar 24. If the carrier bar has more than four pockets, i.e., 30 pockets as shown in the carrier bars of FIGS. 6 and 7, eight camera units would be needed to sense the plurality of pockets simultaneously (one camera unit for every four pockets). However, it is contemplated that the camera units may be configured to monitor any number of pockets provided in each of the carrier bars.

The camera units 48, 50 may be configured to sense any other predetermined characteristic of the pellet-shaped article. For example, the camera units 48, 50 may be configured to sense a particular indicia and/or color appearing on the pellet-shaped article. If the indicia and/or color of the pellet-shaped article does not fall within the predetermined range of the camera units 48, 50, then that particular pellet-shaped article will be removed by the removal mechanism 46 from the conveyer mechanism 12. Alternatively, if the indicia and/or color of the pellet-shaped article falls within the predetermined range of the camera units 48, 50, meaning that the pellet-shaped article is properly marked and/or colored, then that particular pellet-shaped article is not removed by the removal mechanism 46. Each camera unit may detect that an article is not contained with the carrier bar or feed drum. In that event, it is preferable to abstain from performing any processing at that particular location, to thereby prevent potential damage to the conveyer apparatus. For example, the laser may cause damage to the carrier pocket or feed drum if no article is present. Where the carrier bar or feed drum has no article and the processing still takes place, the provision of throughholes in the carrier bar or feed drum will prevent damage in the vent processing, e.g., lasering, occurs inadvertently.

Further, the camera units 48, 50 may be configured to sense different characteristics from one another. For example, the first camera unit 48 may be configured to sense indicia and to sense if the pellet-shaped article has been properly coated. The second camera unit 50 may be configured to sense only if the pellet-shaped article has been properly coated. This configuration can help speed processing time.

As shown in FIG. 9, the first camera unit 48 is positioned transverse to the carrier bars 24 on an upper side of the conveyer mechanism 12 to sense one side of the tablet-shaped article 44. The second camera unit 50 is positioned transverse to the carrier bars 24 on an inner side of the conveyer mechanism 12 to sense the other side of the tablet-shaped article 44. As a result, both sides 45, 47 of the tablet-shaped articles 44 are sensed by the first and second camera units 48, 50 as the tablet-shaped articles 44 pass thereby. The camera unit 50 is able to sense the downwardly facing side of the tablet-shaped article 44 due to the throughholes 36 in each of the pockets 34 of the carrier bars 24.

Figure 9A:
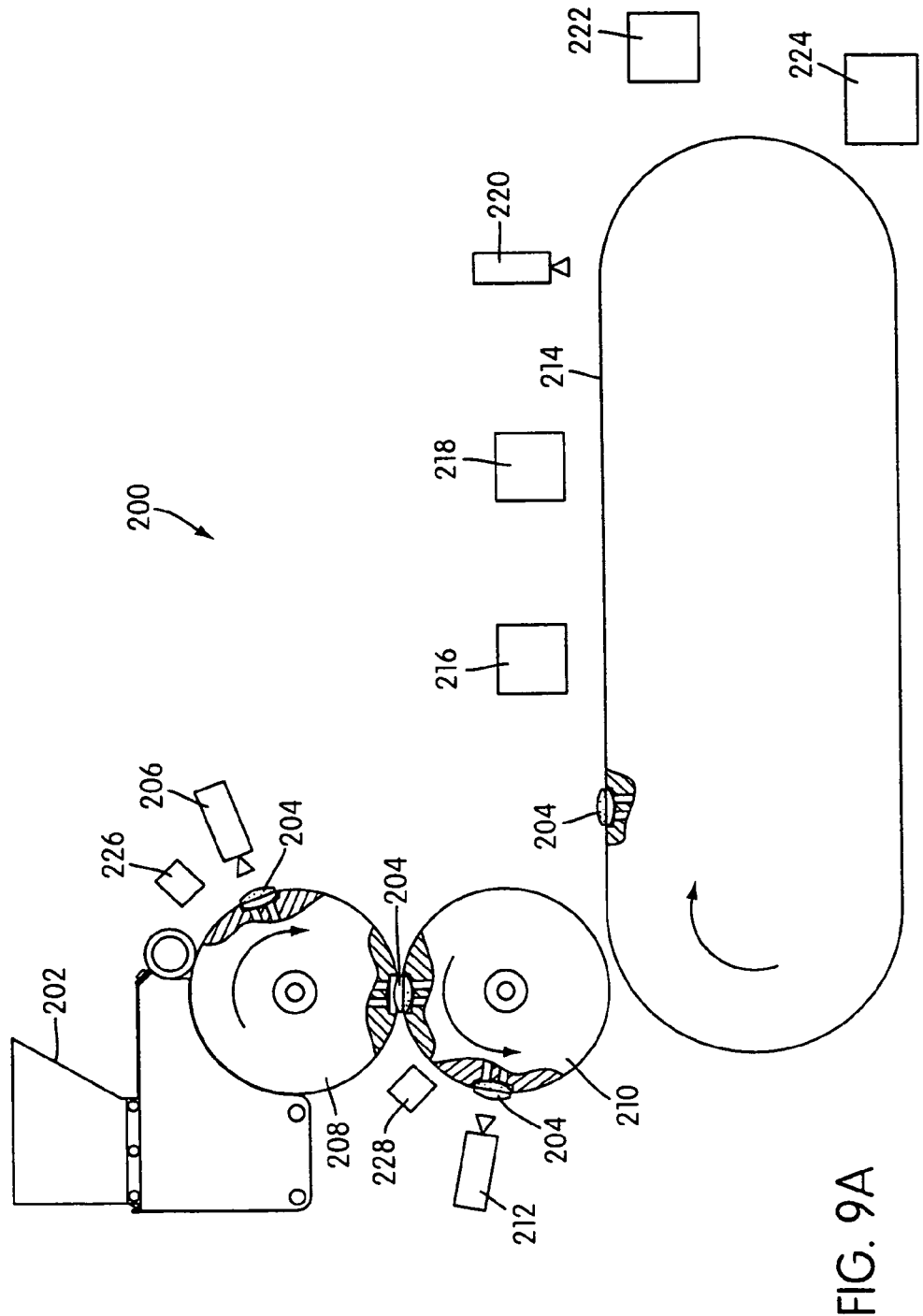
FIGS. 9A and 9B are alternative embodiments of the present invention.
Figure 9B:
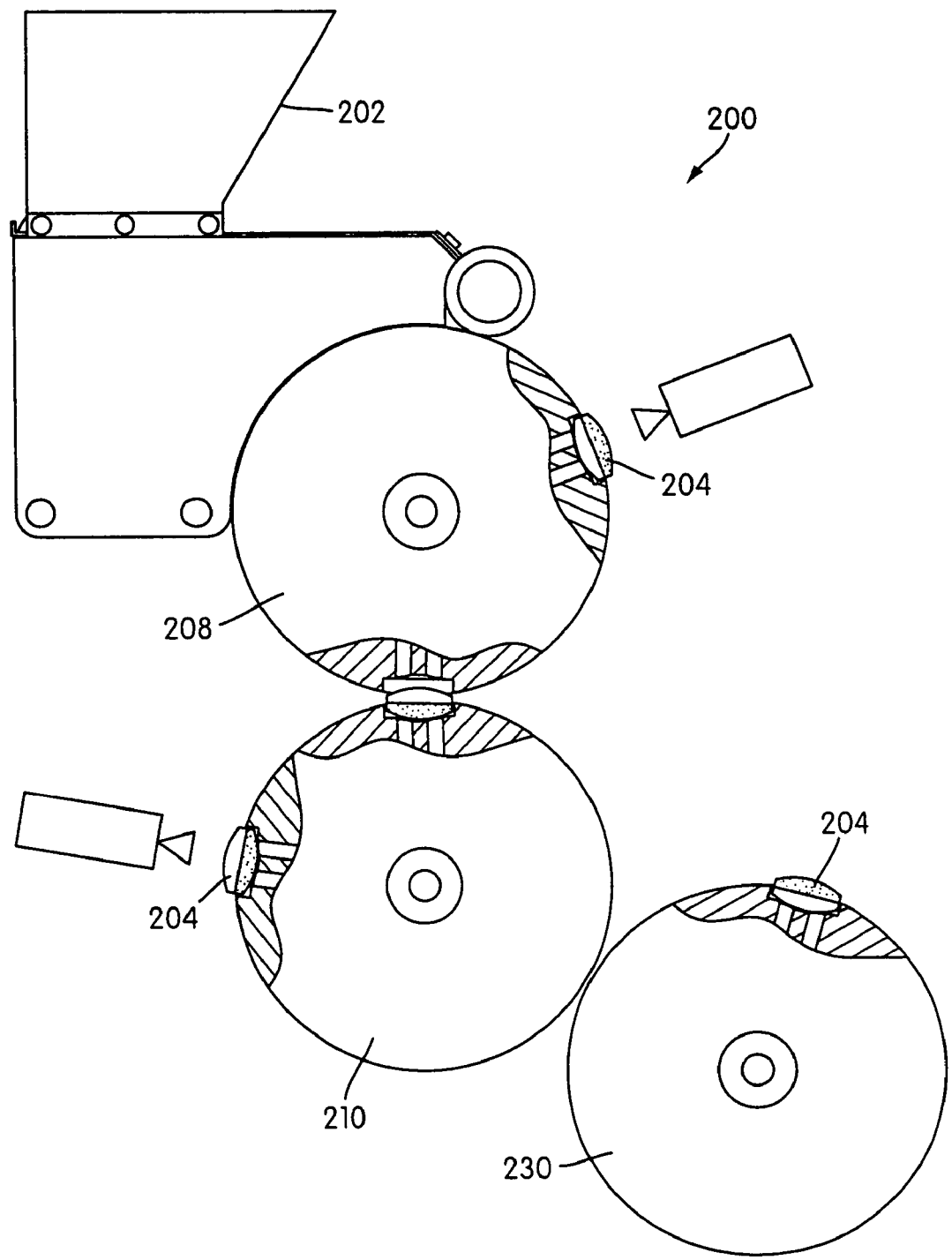

A drum feed printer can also be used to sense the sides of an article or tablet. For example, the product can be flipped over when being transferred from one drum to another drum. FIGS. 9A and 9B illustrate two embodiments of a drum feed system in accordance with the present invention. As shown in FIG. 9A, a drum feed system 200 includes a hopper 202 containing a plurality of articles to be processed, e.g., drilled, inspected, provided with indicia, etc., on one or both sides. Articles 204 from the hopper 202 have first and second sides with first and second predetermined characteristics that may be different from one another. For example, the sides may have a different color, and/or both sides may have a coating. A first camera unit 206 is provided to sense the first side of the article as it is carried by a first feed drum 208 converging the article along a conveying path. A second feed drum 210 receives the article A from the first feed drum 208 to expose the second side of the article A to processing. A second camera unit 212 inspects the second side of the article. The second feed drum 210 feeds the article to a conveyer mechanism 214, similar to that described below in relation to FIG. 17. The conveyer mechanism 214 may include one or more processing stations 216, 218, an inspection unit 220 or camera, and suitable reject and accept bins 222, 224 like those shown in FIG. 17. Further processing stations 226, 228 may be provided on the first and second feed drums 208, 210, respectively. For example, processing stations 226, 228 may provide coatings to the first and second sides of the article, while the processing station 216 provides indicia, e.g., printing, and the processing station 218 drills holes for time release purposes.

FIG. 9B shows a feed drum system which is similar to that shown in FIG. 9A, and like reference numbers have been used to indicate like parts. However, the first feed drum 208 in FIG. 9B receives the articles 204 in a manner that seats the articles generally in the correct position. The articles are more accurately seated in the second feed drum 210, while a third feed drum 230 serves to re-expose the first side of the article for inspection/processing.

In the illustrated embodiment, the camera units 48, 50 are staggered along the conveying path due to physical limitations on the inner side of the conveyer mechanism 12. Specifically, as shown in FIG. 9, the conveyer mechanism 12 is in the form of a continuous chain conveyer 20 disposed upon appropriately positioned sprockets 22. The chain conveyer 20 is constructed and arranged to releasably mount the carrier bars 24 for collecting pellet-shaped articles from the feed hopper 18 and for conveying the collected pellet-shaped articles through the inspection unit 10. The carrier bars 24 may be releasably mounted to the chain conveyer 20 in any suitable method. For example, the chain conveyer 20 may include a mounting platform that includes a quick-release pin for releasably mounting each of the carrier bars 24, as disclosed in U.S. Pat. No. 5,630,499, which is incorporated herein by reference.

In the illustrated embodiment, the chain conveyer 20 forms the conveyer path that progresses along an incline portion 26 extending from the feed hopper 18 to a generally horizontal portion 28 and through a declining portion 30 where the pellet-shaped articles are discharged. However, the chain conveyer 20 may have different configurations depending on the desired placement of the inspection unit 10 and other units such as the marking apparatus 14. A motor unit 32 is provided to operate the chain conveyer 20 in a predetermined direction. As a result of the above configuration, the positioning of the camera unit 50 is limited due to the positioning of the sprockets 22 of the conveyer mechanism 12. Likewise, the positioning of the camera unit 48 is limited due to the positioning of the marking apparatus 14 that is positioned upstream therefrom. As a result, the camera units 48, 50 sense one side of the pellet-shaped articles at a time. Alternatively, the camera units 48, 50 may be aligned such that the camera units 48, 50 sense respective sides of the pellet-shaped articles simultaneously.

Figure 11:
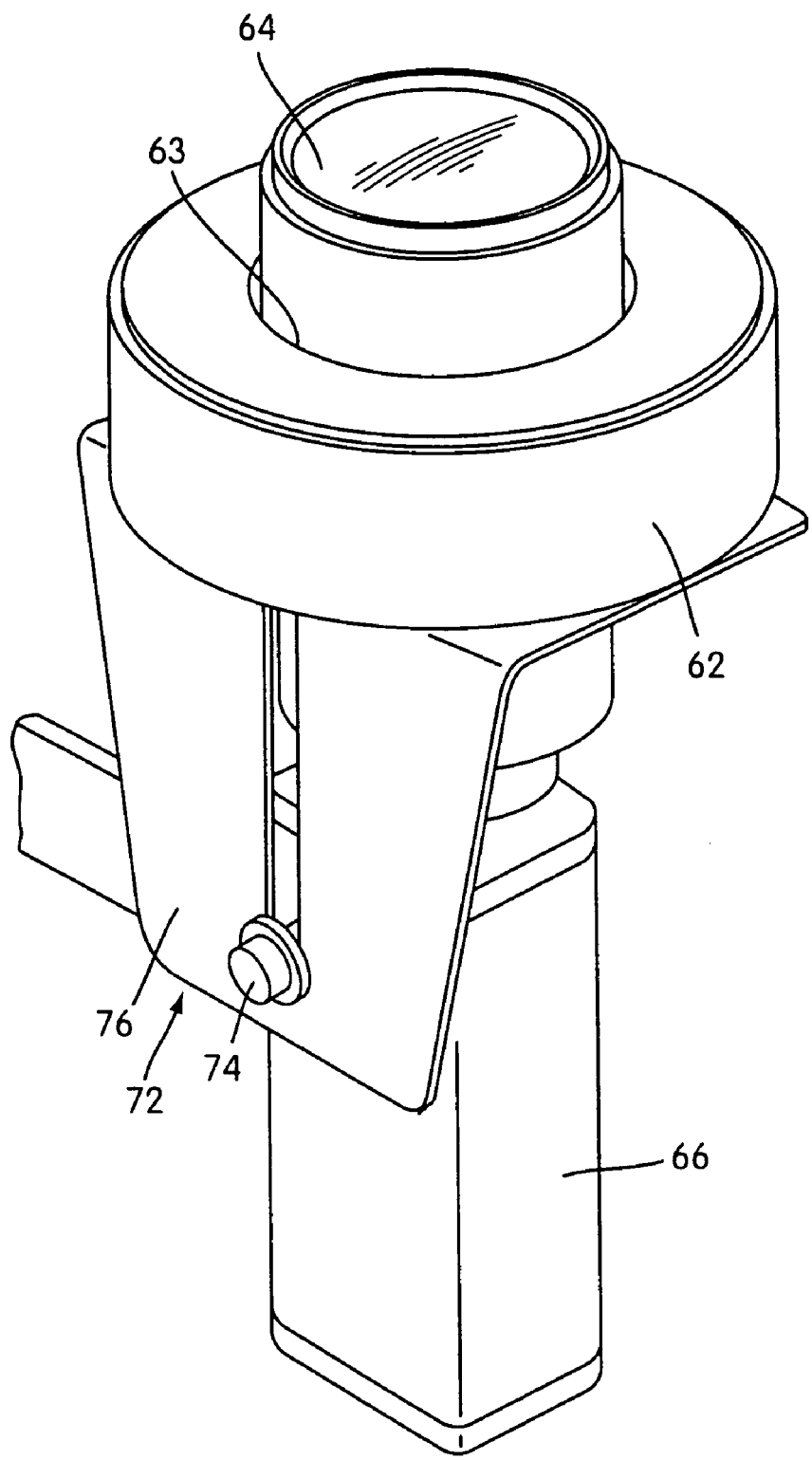
FIG. 11 is an enlarged perspective view of a camera unit of the inspection unit shown in FIG. 9, according to an exemplary embodiment of the present invention.

As best shown in FIG. 11, each camera unit 48, 50 in this example includes a ring light 62, a lens 64, and a ⅓ black/white or color CCD 66. The ring light 62 of each camera unit 48, 50 has an opening 63 therethrough and is configured and positioned to properly illuminate the respective side of the pellet-shaped article as it is being sensed. The lens 64 extends through the opening 63 in the ring light 62 and is coupled to the black/white ⅓ CCD 66. The lens 64 includes a filter configured to separate image data into the color components thereof. In general, light enters the lens 64 and hits the CCD 66, where it is captured by photo-detectors arranged in a mosaic-like pattern. A filter is provided for the lens to allow just one color or selected colors to pass through. The controller 60 has electronic circuitry that interpolates "missing" colors for each pixel. Of course, different lighting systems can be used, depending on the configuration of the article and the predetermined characteristic being sensed. For example, when inspecting for the quality and/or accuracy of the placement of indicia, e.g., printing, the light system should preferably be positioned so as to avoid the creation of shadows, e.g., the light beam should be substantially normal or perpendicular to the article having the indicia. If the predetermined characteristic being inspected relates to the topography or contour of the article, it may be more preferable to angle the light beam with respect to the article, so that a detectable shadow is created to indicate the pressure or absence of a defect that would require removal/acceptance of the article.

Further, each camera unit 48, 50 is mounted to a mounting bracket 72 that is adjustable relative to the conveyer mechanism 12. Specifically, the mounting bracket 72 has a slide 74 that is rigidly connected to each camera unit 48, 50 and a mounting structure 76 that is secured to the frame 12. The slide 74 is slidably engaged within a slot provided in the mounting structure 76 such that the slide 74 and hence each camera unit can move in fore and aft directions with respect to the mounting structure 76 and hence the conveyer mechanism 12. As a result, the camera units 48, 50 can be adjusted with respect to the conveyer mechanism 12 for optimal performance.

The camera units 48, 50 provide signals to the controller 60 (FIG. 12), which signals the removal mechanism 46 so that specified pellet-shaped articles can be removed from the conveyer mechanism 12. Specifically, if either one of the camera units 48, 50 detects the predetermined characteristic (e.g., the color white indicating an improperly coated pellet-shaped article), a signal is provided to the controller 60 which signals the removal mechanism 46 to remove the specified pellet-shaped article from the conveyer mechanism 12.

If the pellet-shaped article is determined to be defective (e.g., not properly coated), the pellet-shaped article is discharged from the respective carrier bar 24 by the removal mechanism 46 that operates in combination with the series of throughholes 46 provided in the carrier bars 24. In the illustrated embodiment, the removal mechanism 46 is positioned on an inner side of the conveyer mechanism 12 and is appropriately timed to operation of the conveyer mechanism 12 to effectively discharge the specified pellet-shaped articles from the pocket 34 of the carrier bar 24 as the carrier bar 24 passes thereby.

Figure 12:
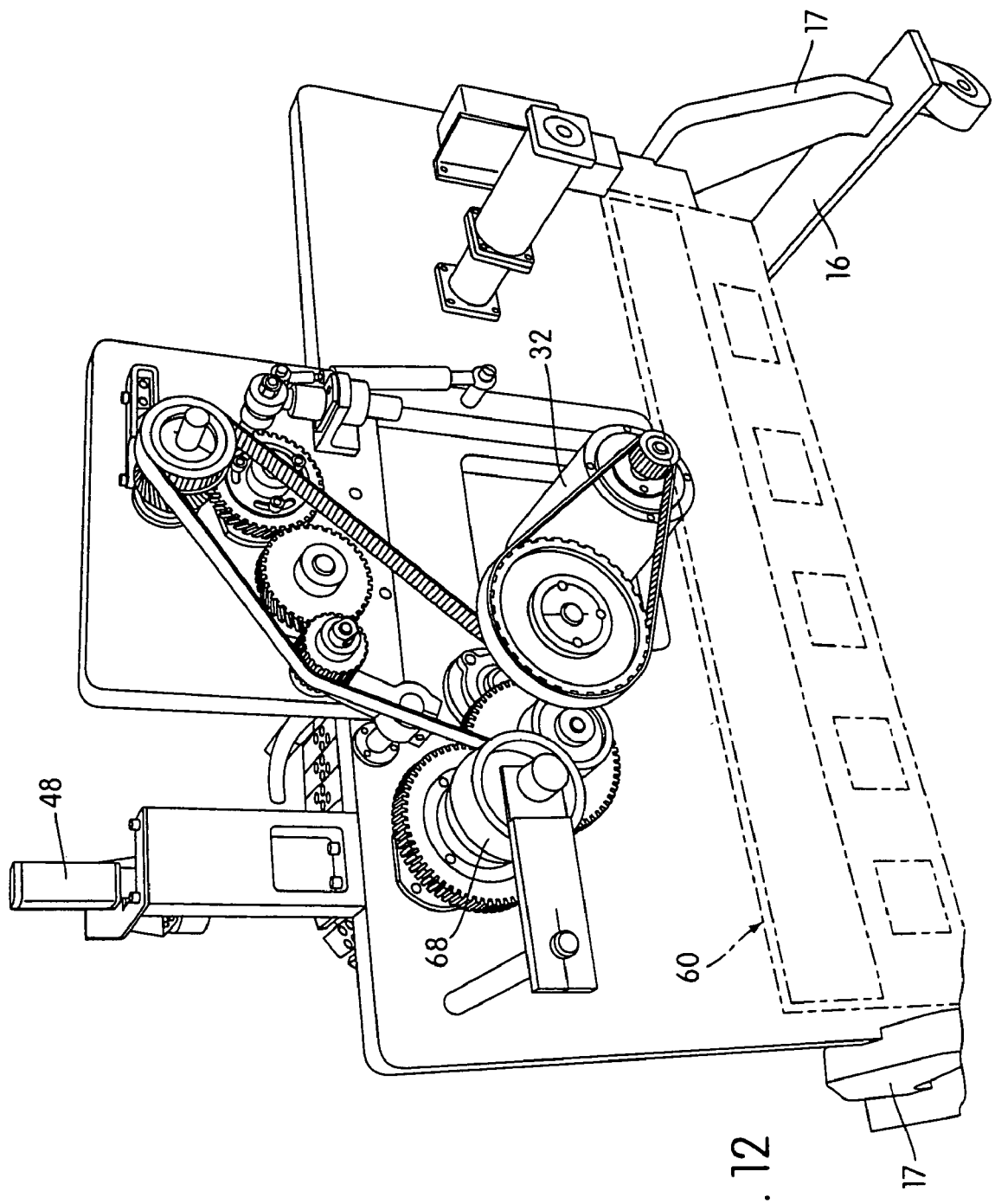
FIG. 12 is a rear perspective view of the conveyer apparatus shown in FIG. 1 illustrating a controller and a conveyer drive mechanism.

Specifically, the controller 60 is in the form of a program logic control ("PLC") as shown in FIG. 12. The PLC controls operation of the conveyer mechanism 12, inspection unit 10, and marking apparatus 14. As is known in the art, the PLC 60 is linked with an encoder 68 that identifies the exact position of each pellet-shaped article along the conveyer path so that the marking apparatus 14, the camera units 48, 50, and the removal mechanism 46 are appropriately controlled to perform their intended function.

For example, the PLC 60 receives signals from the camera units 48, 50 regarding whether each pellet-shaped article includes the predetermined characteristic. The PLC 60 also receives signals from the encoder 68 to associate the position of each pellet-shaped article with the results from the camera units 48, 50. If the predetermined characteristic is sensed by the either one of the camera units 48, 50, the PLC 60 sends the removal mechanism 46 a signal that includes positional information from the encoder 68 to remove the specified pellet-shaped article from the carrier bar 24.

The PLC 60 may be replaced with a computer system configured to control operation of the conveyer mechanism 12, inspection unit 10, and marking apparatus 14 in a similar manner as described above. The inspection process may be implemented on a programmed general purpose computer. However, the inspection process can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowchart shown in FIG. 16 (as will be discussed below), can be used to implement the inspection process.

The removal mechanism 46 is preferably in the form of a blower. Specifically, the removal mechanism 46 includes a compressor having a plurality of blower nozzles. The compressor may be separate from or part of the unit. The number of blower nozzles is equal to the number of pockets 34 in each carrier bar 24. As a result, one or more specified pellet-shaped articles from each carrier bar 24 may be removed from their respective pocket 34 as it passes by the removal mechanism 44 by selectively controlling the plurality of blower nozzles. If a pellet-shaped article is determined to be defective, the throughhole 36 in the carrier bar 24 is configured to permit a burst of compressed air from a blower nozzle to pass through the throughhole 36 which removes the individual pellet-shaped article from that pocket 34 in the carrier bar 24. The removal mechanism 46 discharges the specified pellet-shaped article into the first bin 54 that is in the form of a reject bin for collecting defective pellet-shaped articles. Thus, the carrier bars 24 convey a plurality of pellet-shaped articles past the inspection unit 10 and selected ones of these pellet-shaped articles within a selected carrier bar 24 can be selectively removed by the removal mechanism 46.

Alternatively, the removal mechanism 46 may be in the form of a plurality of mechanical fingers. The number of mechanical fingers is equal to the number of pockets 34 in each carrier bar 24. Similar to the above, one or more specified pellet-shaped articles from each carrier bar 24 may be removed from their respective pocket 34 as it passes by the mechanical fingers by selectively actuating the mechanical fingers.

Figure 13:
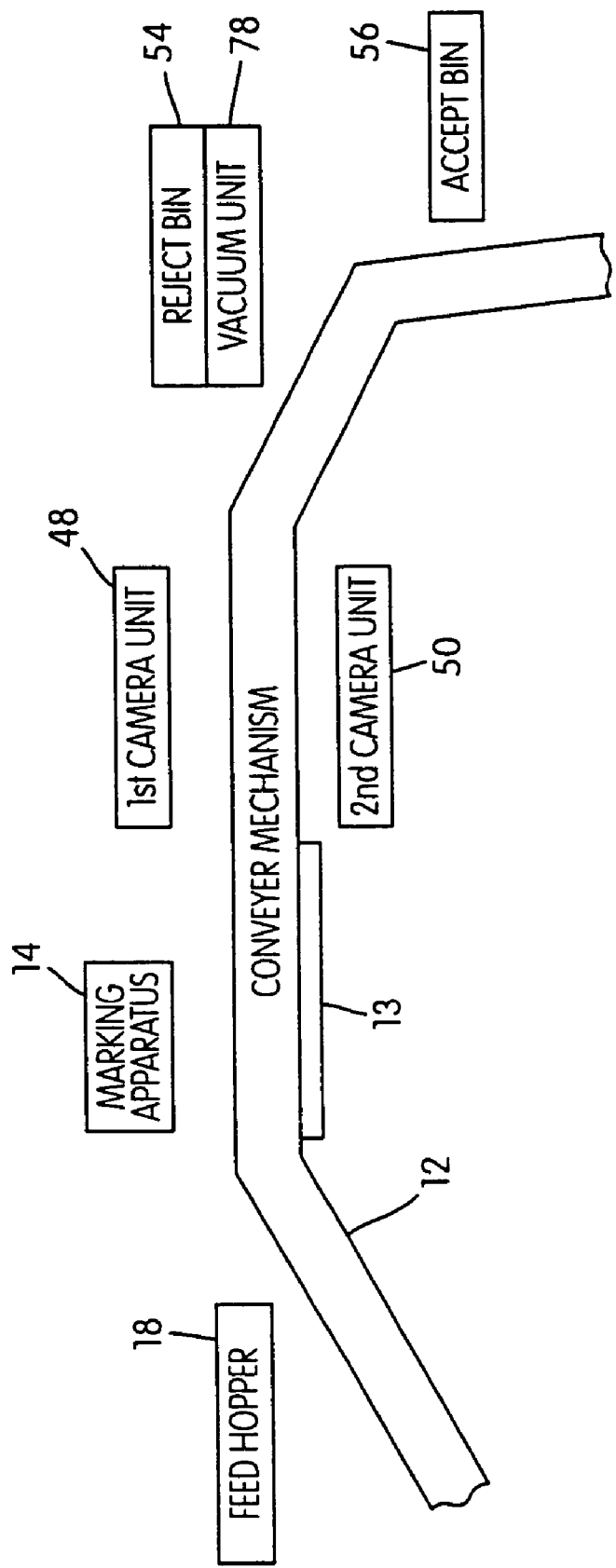
FIG. 13 is a schematic view illustrating an inspection unit having a vacuum unit, according to an embodiment of the invention.

Alternatively, the removal mechanism 46 may be in the form of a vacuum unit 78, as shown in FIG. 13. The vacuum unit 78 is positioned on an upper side of the conveyer mechanism 12 following the camera units 48, 50. The vacuum unit 78 may be configured to draw in specified pellet-shaped articles from the carrier bars 24 that are determined to be defective and collect the defective pellet-shaped articles in a reject bin 54. The vacuum unit 78 and the reject bin 54 may be formed as an integral unit If the pellet-shaped articles are acceptable, they are deposited into an accept bin 56. The vacuum unit 78 may be secured to the frame 12 in any suitable manner.

Further, the conveyer mechanism 12 may be provided with a suitable vacuum hold down unit 13. For example, the vacuum hold down unit 13 may be provided below the conveyer mechanism 12 as shown in FIG. 13. The vacuum hold down unit 13 helps to maintain the articles in a predetermined position during processing of the articles along the conveyer path, especially when the articles are subject to multiple operations requiring registration from one processing unit to the next. The vacuum hold down unit should preferably extend below those processing units on the horizontal extent of the conveyer mechanism 12. The vacuum hold down unit 13 can be integrated with the second camera unit 50. The vacuum hold down unit 13 may draw in air via the holes in the carrier bars or the feed drum, as shown in FIG. 9A.

In the illustrated embodiment, the camera units 48, 50 are positioned along the horizontal portion 28 of the conveyer path. However, the camera units 48, 50 may be positioned along the incline portion 26 following the feed hopper 18 or any other position along the conveyer path that follows the feed hopper 18 and precedes the removal mechanism 46. In the illustrated embodiment, the removal mechanism 46 is positioned along the declining portion 30. However, the removal mechanism 46 may be positioned on any portion of the conveyer path that follows the camera units 48, 50. Further, the removal mechanism 46 is positioned on the inner side of the conveyer mechanism 12 when it is in the form of a blower or mechanical fingers in order to discharge selected pellet-shaped articles into the reject bin 54. The removal mechanism 46 is positioned on the upper side of the conveyer mechanism 12 when it is in the form of a vacuum unit 78 in order to draw in selected pellet-shaped articles into the integral reject bin. Moreover, if a vacuum unit 78 is utilized and only the first camera unit 48 is utilized to sense one selected side of the pellet-shaped articles (e.g., inspect indicia only), it is not necessary to provide throughholes 36 in the carrier bars 24.

As mentioned above, it is contemplated that a single camera unit may be provided to sense a predetermined characteristic of the pellet-shaped article. For example, a single camera unit may be provided to sense only one selected side of the pellet-shaped article for the predetermined characteristic. The camera unit may be provided on either the inner side of the conveyer mechanism 12 or the upper side of the conveyer mechanism 12. It may be advantageous to position a single camera unit on an inner side of the conveyer mechanism 12 to make the system more compact and provide an isolated atmosphere to enhance the sensing capability of the camera unit. Specifically, a camera unit on an inner side of the conveyer mechanism 12 is insulated from ambient light to provide more accurate readings.

Figure 14:
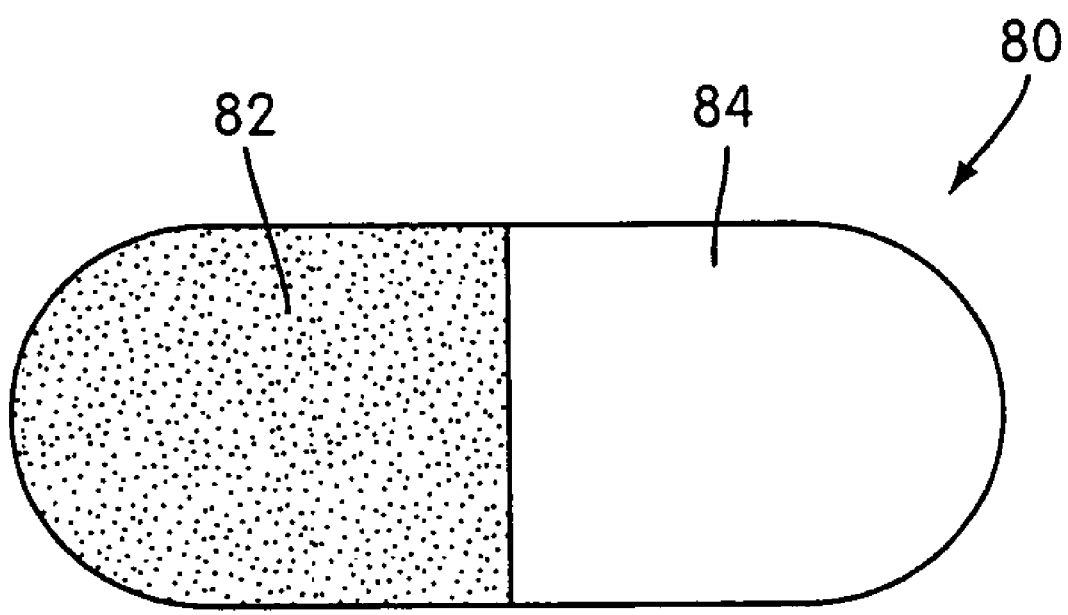
FIG. 14 is a perspective view illustrating a caplet-shaped article.

For example, FIG. 14 shows a pellet-shaped article in the form of a caplet 80 having a first end 82 and a second end 84. The ends 82, 84 typically have different colors. Only a single camera unit is needed to read one side of the caplet 80 in order to determine if the ends 82, 84 are properly colored. If the camera unit is provided on the inner side of the conveyer mechanism 12, the carrier bars 24 must have throughholes 36 in order to sense the caplet 80. If the camera unit is provided on the upper side of the conveyer mechanism 12, the carrier bars 24 may or may not have throughholes 36 depending on the configuration of the removal mechanism 46. For example, throughholes 36 are needed for the blower embodiment and throughholes 36 are not needed for the vacuum unit embodiment, as discussed above. Moreover, the inspection unit 10 may be used for a three-drum printer, an example of which is described in Ackley's U.S. Pat. No. 6,286,421. For example, the camera unit may be positioned on an inner side of one of the drums with the removal mechanism at a position following the camera unit. The three-drum printer need not spin the article, as described in the '421 patent.

As aforesaid, the marking apparatus 14 is provided along the same conveying path as the inspection unit 10. In the illustrated embodiment, the marking apparatus 14 precedes the inspection unit 10. However, the marking apparatus 14 may follow the inspection unit 10 if the indicia is not to be inspected, or may not be provided at all. Alternatively, the inspection unit 10 can be programmed to sense only the coating even if the marking apparatus 14 is provided. Further, a marking may be applied to the pellet-shaped articles by a process other than the marking apparatus 14 (e.g., during coating). Consequently, the inspection unit 14 can inspect the marking on a pellet-shaped article even if a marking apparatus 14 is not provided.

Figure 15:
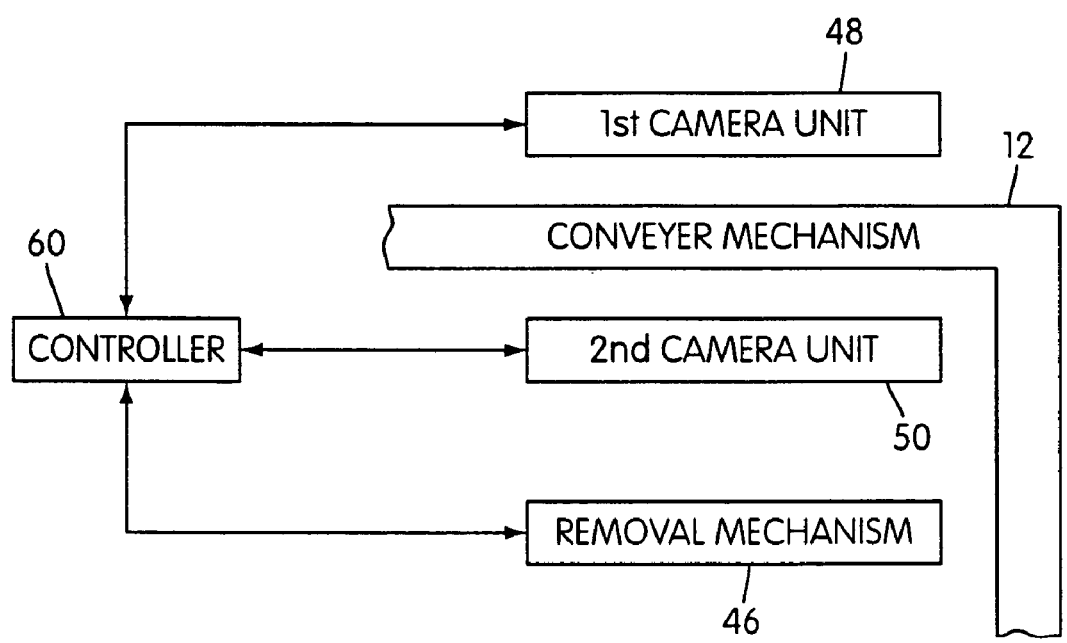
FIG. 15 is a schematic view illustrating the association between components of the inspection unit.

Operation of the inspection unit will now be described in greater detail. After the carrier bars 24 and the pellet-shaped articles pass beneath the brush 52 and the blow-back members 58, the carrier bars 24 and the pellet-shaped articles encounter the marking apparatus 14 where the pellet-shaped articles are marked with desired indicia. As mentioned above, the marking apparatus 14 may not be provided. Following the marking apparatus 14, the carrier bars 24 pass by the first and second camera units 48, 50 of the inspection unit 10. The camera units 48, 50 sense respective sides of the pellet-shaped articles for the predetermined characteristic. If a defective pellet-shaped article is detected (e.g., not properly coated), the camera units 48, 50 provide a signal to the controller 60 which signals the removal mechanism 46. The controller 60 directs the removal mechanism 46 to remove the specified pellet-shaped article from the carrier bar 24. Alternatively, a single camera unit may be provided to sense for the predetermined characteristic and to signal the controller 60 which signals the removal mechanism 46 to remove the specified pellet-shaped article from the carrier bar 24. FIG. 15 is a schematic view that illustrates the association between the controller 60, the first and second camera units 48, 50, and the removal mechanism 46.

Figure 16:
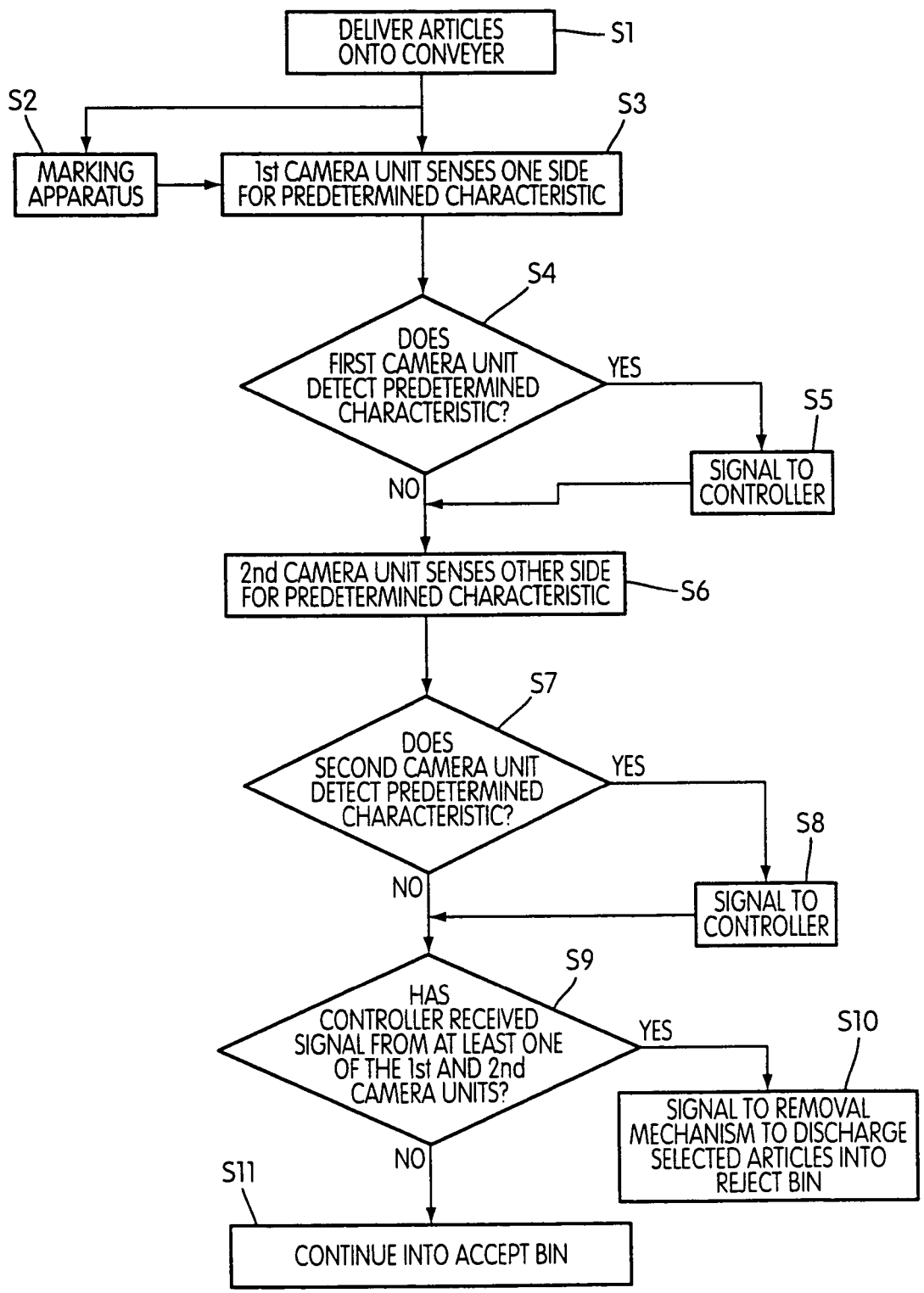
FIG. 16 is a flow chart illustrating an embodiment of the inspecting and removing process of the inspection unit.

More specifically, referring to FIG. 16, the pellet-shaped articles are delivered onto the conveyer mechanism 12 by the feed hopper at step S1. A marking apparatus 14 may be provided along the conveyer path. In the illustrated embodiment, the conveyer mechanism 12 passes by the marking apparatus 14 at step S2. At step S3, the carrier bars 24 of the conveyer mechanism 12 pass by the first camera unit 48 that senses one side of the pellet-shaped article for the predetermined characteristic. If the first camera unit 48 detects the predetermined characteristic at step S4, a signal is provided to the controller 60 at step S5 to remove that individual pellet-shaped article. The carrier bars 24 continue along the conveyer path and pass by the second camera unit 50 at step S6 that senses the other side of the pellet-shaped article for the predetermined characteristic. If the second camera unit 50 detects the predetermined characteristic at step S7, a signal is provided to the controller 60 at step S8 to remove that individual pellet-shaped article. If at least one of the camera units 48, 50 detects a defective pellet-shaped article, a signal is provided to the controller 60 to remove that specified pellet-shaped article.

After passing by the first and second camera units 48, 50, the conveyer mechanism 12 will cause the pellet-shaped articles to progress to the declining portion 30 of the conveyer path. If the pellet-shaped article is determined to be defective by either one of the camera units (i.e., the controller 60 has received a signal from at least one of the first and second camera units 48, 50) at step S9, the controller 60 signals the removal mechanism 46 positioned adjacent the declining portion 30 to remove the specified pellet-shaped article at step S11. Specifically, the removal mechanism 46 discharges the specified pellet-shaped article into the reject bin 54 where defective pellet-shaped articles are collected. If the pellet-shaped article is not defective (i.e., the controller 60 has not received a signal from either of the camera units 48, 50), the pellet-shaped article continues down the declining portion 30 until it falls out under the influence of gravity and continues along a path to the second bin in the form of an accept bin 56 (shown in FIGS. 1 and 2) at step S11 where non-defective pellet-shaped articles are collected. Alternatively, the non-defective pellet-shaped articles may continue along a path to an adjacent conveyer mechanism that transports the accepted or non-defective pellet-shaped articles to a further processing operation. The system may include an additional discharge mechanism to facilitate the discharge of non-defective pellet-shaped articles from pockets of the carrier bars 24.

As indicated in FIG. 16, rejected articles are actively rejected whereas accepted articles are passively accepted. In another embodiment, the accepted articles can be ejected into an accept bin (active acceptance), while the rejected articles are allowed to remain in the conveyer to be transported into a reject bin (passive rejection).

FIGS. 17-24 illustrate another embodiment of the present invention. It is to be understood that various components described below may be included within the embodiments described above, and various components described above may be used in conjunction with the components described below.

Figure 17:
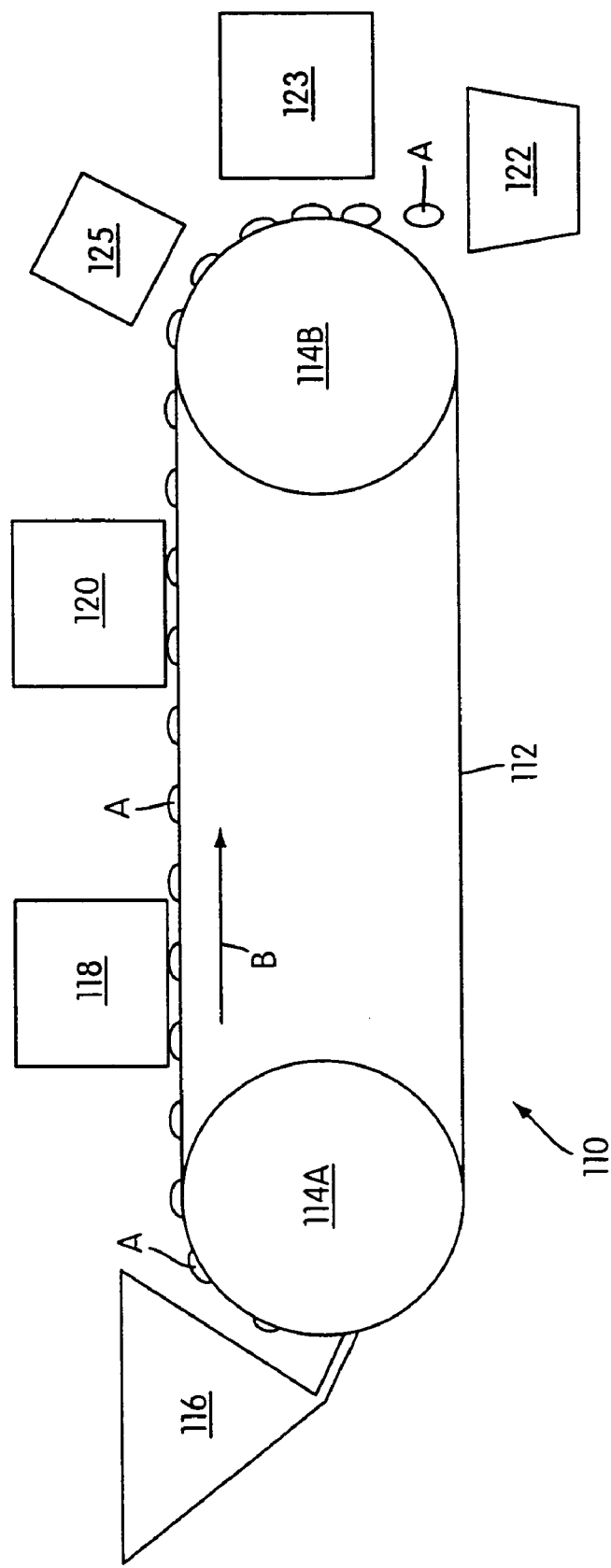
FIG. 17 is a schematic view of an apparatus to convey pellet-shaped articles according to an embodiment of the present invention.

FIG. 17 shows a schematic view of a transporting and processing apparatus 110 according to an illustrative embodiment of the present invention. In one example, the transporting and processing apparatus includes a conveyer loop 112 which is entrained about a pair of sprockets 114A and 114B to travel along a transport path in a direction indicated by an arrow B. Other configurations are also contemplated. A dispenser 116, e.g., a hopper, is disposed over the conveyer loop 112 and dispenses articles onto the conveyer loop 112. The articles can be edible or non-edible including confectioneries, non-confectioneries, candies, food, pharmaceuticals or any other discreet type articles. Several dispensers are well known in the art and may be used in the present invention, including but not limited to hoppers, rollers and feed dispensers. The dispenser 116 is positioned adjacent the sprocket 114A which causes the conveyer loop 112 to follow along a predetermined radius of curvature. The conveyer loop 112 travels around a curvilinear path made up of substantially linear sections and substantially non-linear sections, e.g., where the sprockets 114A and 114B are located.

After the dispenser 116 dispenses the articles to the conveyer loop 112, the articles are transported past one or more processing stations 118 and 120. The processing stations may be drilling stations, printing stations or any other process which can be applied to modify the appearance and/or shape of the articles. The processing stations 118 or 120 perform first and second processes on the articles which are coordinated with another. For example, the first processing station 118 may be a first printer and the second processing station 120 may be a second printer that serially print component images of a composite image on the articles in registered relationship with one another. The processing stations 118 and 120 are located on a portion of the conveyer loop 112 which is substantially linear or not less than a predetermined radius of curvature. The conveyer loop 112 transports the article past the sprocket 114B where the articles are inspected by an inspection unit 125. Following inspection, acceptable and non-acceptable articles are separated from one another. For example, rejected articles may be released into a drop-off or "reject" bin 122, while acceptable articles may be directed to an accept bin (123) or suitable post processing receptacles, such as a blistered package, etc. The conveyer loop 112 follows this cycle to pick up additional articles from the dispenser 116. The articles may be maintained in a predetermined position, e.g., using the system described in U.S. Pat. No. 6,314,876 to Ackley, Jr., incorporated herein by reference in its entirety.

The above embodiment is only for the purposes of illustration, as other configurations for the transport loop are within the scope of the invention. For example, the ramp-type conveyer described in FIG. 1 can include the systems describe above in FIG. 17, or a drum feed system could be employed.

Figure 18:
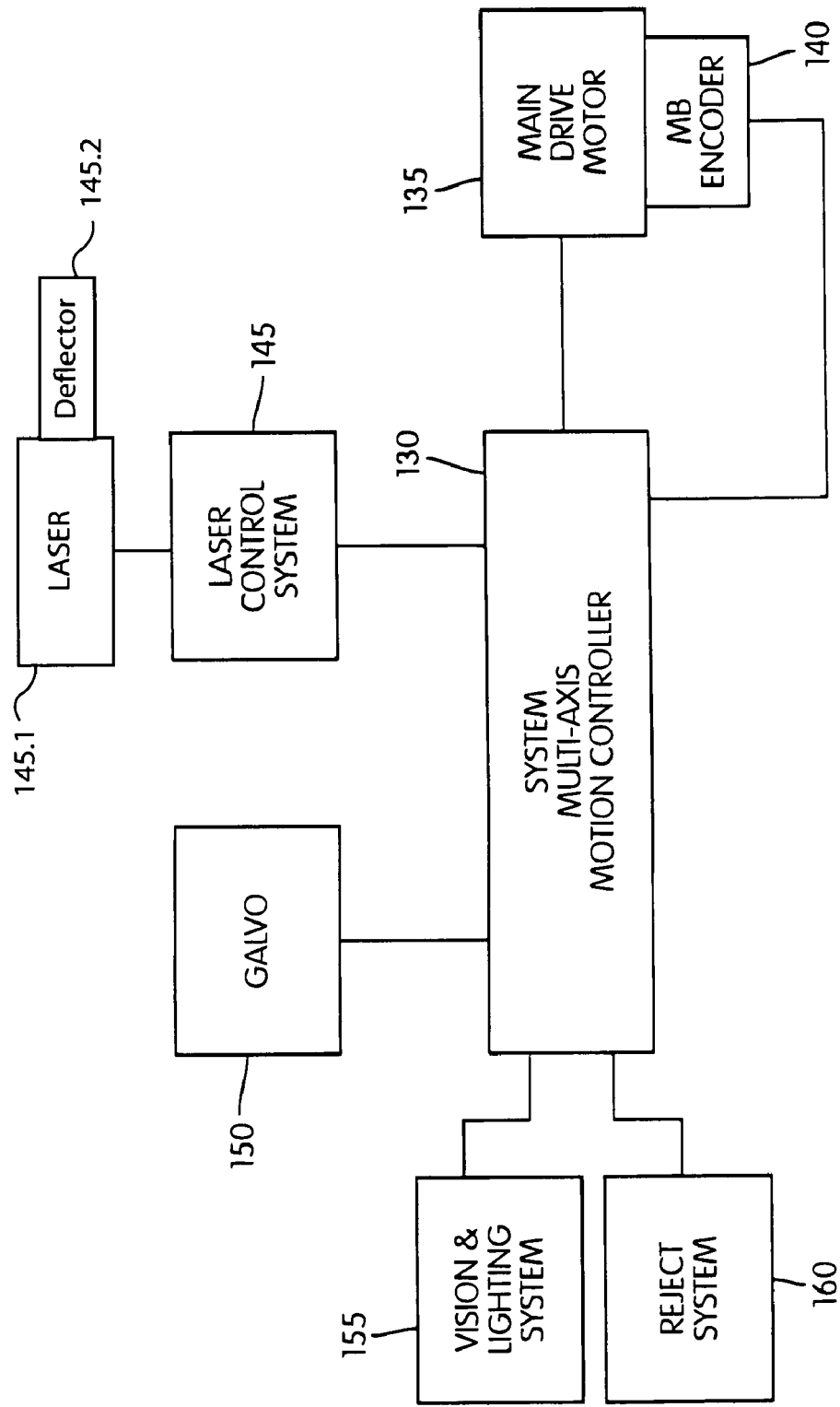
FIG. 18 is a schematic view of control system for drilling and/or inspection of drilled holes in a pellet-shaped article, according to an embodiment of the present invention.

FIG. 18 is a schematic diagram showing a control system for use with a conveying apparatus as described above. A controller 130, e.g., in the form of a CPU, personal computer or a programmable logic control unit, coordinates various components of a laser control system and an inspection unit. A main drive motor 135 is operatively coupled, e.g., to one of the sprockets 114A or 114B (FIG. 17) to transport the articles from station to station along the transport path. The drive motor 135 is preferably designed to continuously drive the conveyer loop 112. An encoder 140 is coupled to the motor 135 and provides a signal to determine the position of the articles on the transport loop 112 relative to the processing stations 118 and 120.

A laser control system 145 and a galvanometer 150 are in communication with the controller 130. The laser control system 145 controls a laser 145.1 such as commercially available from Coherent, model no. Diamond K-250. Laser 145.1 may be associated with a deflector 145.2 to split the laser beam into a plurality of beams directed to articles provided in spaced rows. The galvanometer is also commercially available from GSI Lumonics, model no. HSM15M2. These components are provided to drill laser holes in the articles A. However, it is to be understood that the above laser and galvanometer are exemplary only, and that other lasers and galvanometers can be used as well.

A vision and lighting system 155 and reject system 160 are also in communication with the controller 130, to provide an active system to inspect articles after one or more processing operations and to actively accept selected ones of articles which are found to meet predetermined requirements programmed into or accessible to the controller 130. The vision and light system 155 and the reject system 160 together can be considered to constitute an inspection unit, in one example. The controller 130 may be programmed to control multiple lasers, laser control systems, galvos and/or vision and reject systems.

Laser System

FIG. 19 shows one example of an article A which is round, although the article could be a caplet as well. The article A has a depth, diameter and shape which may vary. The article A is provided with a laser hole 165, which is shown on an enlarged scale in FIG. 19A to include minimum and maximum diameters indicating the acceptable tolerance range of the hole size, as indicated by the inner and outer circles. The diameter of the hole 165 is designed to be in the range of about 50 micrometers to about 1 mm, for smaller holes, and about 1 mm to about 6 mm for larger holes. The depth of the hole is typically in the range of about 450-500 micrometers. The depth of the hole is at least equal to and preferably greater than the thickness of the coating to achieve the desired effect. The depth is controlled by pulsing the laser at least one time, and preferably multiple times in the same position until the depth is proper, as shown in FIG. 20. The diameter of the drilled hole is between the minimum and maximum diameters determined by the acceptable tolerance range of the hole size.

In a first mode, the diameter of the holes is controlled by using a laser to create relatively smaller holes having a diameter in the range of about 50 micrometers to about 1 mm, and preferably about 400-800 micrometers. In a second mode, the same laser is controlled to create a relatively large composite hole using a series of holes in a predetermined pattern, as shown in FIGS. 21 and 22. In FIGS. 21 and 22, a relatively larger diameter hole, e.g., in the range of about 1 mm to about 6 mm, preferably about 3-6 mm, is created by pulsing the laser with smaller diameter holes in different positions to create the large diameter hole. In FIG. 21, the pattern includes seven holes in the general shape of a hexagon, while FIG. 22 shows the pattern to include many more smaller holes, e.g., 37 holes with 4 on each side of a generally hexagonal shaped hole. FIGS. 21 and 22 show that the overall size of the combined holes falls within the tolerance range for the selected hole diameter.

In general the number and size of the holes and the pattern size and shape may vary to create the desired hole diameter. Changing the hole diameter and/or depth affects the surface area of the article exposed to the fluids in the digestive tract, which may be used to better control the release of the medicine. In other words, one inventive concept extends to increasing the surface-area exposed to the fluid in the stomach, regardless of how the increased surface area is achieved. The increased surface area may be uniform or non-uniform cross section. Increased surface area may be achieved via larger drilled holes, or by etching away a portion of the coating using the laser, for example. The increased surface area includes the increased surface area of the walls of the drilled holes, due to the enlarged diameter of the hole.

The conveyer belt, galvo position, and laser are all controlled by the same control unit. It is a multi-axis motion controller with sophisticated move profile controls. The conveyer belt has encoder feedback to provide carrier belt position and speed information to the system. The galvo has two mirrors mounted to high performance servo motors. The laser pointing is controlled by the mirror positions. The mirror positions are determined by the controller.

In one aspect of the invention the galvo is commanded to point the laser at the center of the tablet and then the controller fires the laser for a set period of time. This period of time combined with the laser pulse width and pulse period will determine the hole depth. For example, each product may be in the vicinity of the laser for a total time of about 50-300 milliseconds (ms), preferably about 100-200 ms, and most preferably 150 ms, depending on the product involved. In that time, the pulse period may be about 400-600 microseconds, e.g., about 500 microseconds, in which the product can be lasered. The pulse width may be about 40-60 microseconds, e.g., about 50 microseconds. In that pulse width, the product may be pulsed 7-8 times to create the proper depth, although the correct depth may be achieved with a single pulse, or more than 7-8 pulses.

In another aspect of the invention, the galvo will be commanded to perform a complex series of moves, while at the same time electronically gearing to the conveyer belt. The controller will command the laser to fire at the appropriate times. The depth of the hole is determined be laser pulse width, pulse period and galvo speed. The diameter of the hole is determined by the software in the controller.

One advantage of this system is that the same laser can be used to create holes having a diameter from about 50 micrometers to about 1 mm for relatively smaller holes, and, for relatively larger holes, the diameter ranges from about 1 mm to about 6 mm. This avoids the need to switch lasers or to buy lasers with a large diameter, which would be expensive.

The laser can also be used to drill holes on a plurality of rows of articles at the same time. The range of motion for the galvo is such that it is able to point at multiple products across the conveyer bed. For example, the laser can be fired at 6 discrete products with ⅝" spacing between the products. The galvo can be commanded to point at each product in sequence and then fire the laser at each.

Inspection

Figure 23:
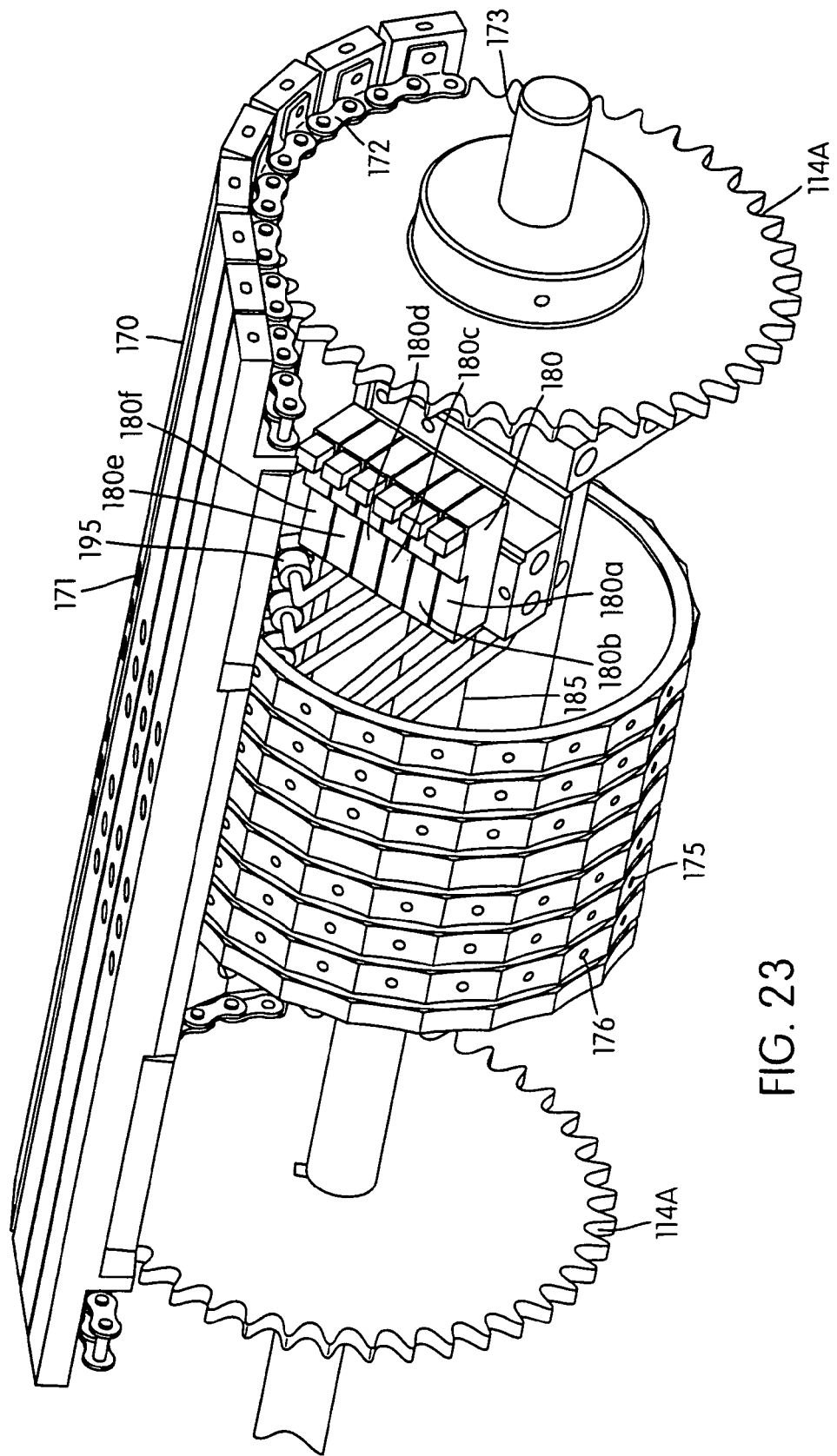
FIG. 23 is a partial cut-away perspective view of a portion of an inspection unit in accordance with an embodiment of the present invention.

FIG. 23 is a partial perspective view of the inside of the conveyer loop 112, which in this example takes the form of a plurality of carrier bars 170 having at least one row and preferably several axially spaced rows, e.g., six, of recesses 171 for receiving articles A. The carrier bars 170 are coupled to a conveyer chain 172 trained about the sprockets 114A and keyed to a common shaft 173.

A drum 175 forming a part of the reject system 160 of the inspection unit is positioned between and rotates with the sprockets 114A about the shaft 173. The drum 175 includes a plurality of holes 176 that are provided in an array of six rows, along the axis of the drum 175, to match the number of axially spaced rows in the carrier bars 170. Further, the holes in the drum 175 are spaced apart a distance, in a circumferential sense, which is about the same as the distance between recesses 171 in adjacent carrier bars. In this example, the holes in both the drum and the carrier bars are through-holes.

Provided inside the drum 175 is a solenoid pack 180 which includes one or more solenoids 180a-180f, in this example, to match the number of axially spaced rows in the drum 175 and carrier bars 170. Each solenoid is associated with a solenoid tube 185, each tube 185 having a fitting 195 coupled to a shoe 190 to which the solenoid pack 180 is mounted. Shoe 190 is better seen in FIG. 24 which for simplicity and clarity does not include the transport loop or sprockets, etc.

Figure 24:
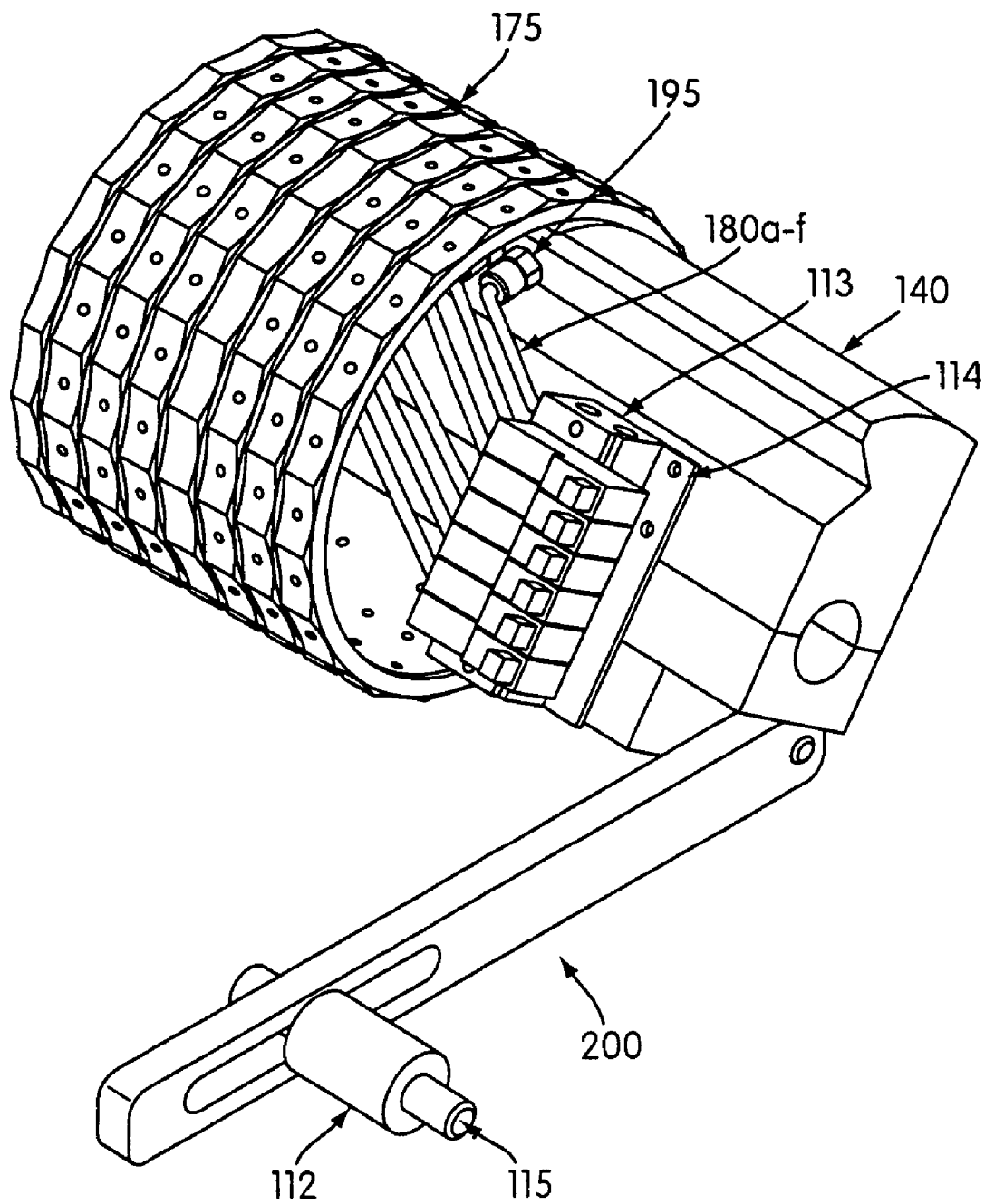
FIG. 24 is a perspective view of a portion of the inspection unit shown in FIG. 23.

FIG. 24 shows that the shape of the shoe 190 is complimentary to the inside surface of the drum 175. Each tube 180 end includes a fitting 195 which is provided to the shoe 190. Shoe 190 includes number of holes, e.g., six, corresponding to the number of axially spaced rows of the drum 175. Shoe 190 is fixedly coupled to the frame of the conveyer such that the drum 175 and carrier bars rotate around the fixed shoe 190. The position of the shoe 190 can be changed using a bracket 200 having a slot with a pin or threaded bolt with optional spacer which can be fastened to the frame.

In operation, the drum 175 rotates with the shaft as the carrier bars 170 are conveyed along the transport path. As the carrier bars 170 pass over the drum 175, the holes 176 of the drum 175 register with the recesses 171 of the carrier bars 170. If the articles within the recesses 171 are determined to be acceptable, then the solenoid associated with the article in its recess 171 is activated, e.g., to release a burst of pressurized air (from a pressurized air source) which forces the articles away from the recesses and into an appropriate collection bin for acceptable articles. For any articles that are not acceptable, the solenoid is not activated and the article continues to rotate with the carrier bar until gravity allows the article to be released into a "reject" bin, e.g., bin 22 (FIG. 17).

Although it is contemplated that rejected articles, instead of accepted articles, can be forced out of the recesses 171, the more preferable system includes forcing the accepted articles away from the recesses (active acceptance/passive rejection). In particular, solenoids which are only occasionally activated need more lead time than a solenoid which is continuously and repeated activated. Thus, it is thought that the better approach is to passively allow the rejected articles to be removed from the conveyer, e.g., by gravity, and to actively accept the accepted articles. Stated differently, it is easier and faster to deactivate a solenoid for a rejected article than it is to activate a solenoid for a rejected article. Further, it is also desirable to passively reject so that a failed solenoid will not cause the system to output failed products.

An inspection camera of the type disclosed in the embodiment of FIGS. 1-16 can be used to provide a signal which can be compared to a predetermined standard, to determine whether the article is acceptable or not acceptable. The camera may be mounted outside the conveyer loop to inspect one side of the article. Alternatively or in addition, a second camera can be mounted inside the conveyer loop, e.g., within the drum 175. The signal from the camera can be used to determine the acceptability of a number of characteristics of the article, besides the dimensions of the drilled holes, e.g., logo placement, coating, etc.

It can thus be appreciated that the objectives of the present invention have been fully and effectively accomplished. The foregoing specific embodiments have been provided to illustrate the structural and functional principles of the present invention and are not intended to be limiting. To the contrary, the present invention is intended to encompass all modifications, alterations, and substitutions within the spirit and scope of the present disclosure.

The invention claimed is:

1. A laser drilling system for pellet-shaped articles comprising:
    a laser; and
    a controller operable in first and second modes to allow the laser to create at least one laser drilled hole in the articles having a diameter spanning a range from about 50 micrometers to about 1 mm in the first mode for a relatively smaller hole, and a diameter spanning a range from about 1 mm to about 6 mm in the second mode for a relatively larger hole, wherein a series of smaller holes are combined by pulsing them in adjacent positions to form the relatively larger hole.

2. The laser drilling system according to claim 1, wherein a depth of the relatively larger or smaller holes is greater than a thickness of a coating of the article.

3. The laser drilling system according to claim 2, wherein the depth of the relatively larger or smaller holes is 450-500 µm.

4. The laser drilling system according to claim 1, wherein the controller is set to control the laser to laser each article for about 30-300 ms with a pulse period of about 400-600 ms and a pulse width of about 40-60 ms.

5. The laser drilling system according to claim 4, wherein the laser is controlled to laser each article for about 100-200 ms.

6. The laser drilling system according to claim 4, wherein the laser is controlled to laser each article for about 150 ms.

7. The laser drilling system according to claim 1, wherein the relatively smaller hole is formed by pulsing the laser one or more times in the same position on the articles.

8. The laser drilling system according to claim 1, wherein the series of smaller holes to form the relatively larger hole has a predetermined pattern or shape.

9. The laser drilling system according to claim 8, wherein the pattern is in the form of a hexagon.

10. The laser drilling system according to claim 8, wherein the series of smaller holes includes at least 5 holes.

11. The laser drilling system according to claim 10, wherein the series of smaller holes includes at least 10 holes.

12. The laser drilling system according to claim 11, wherein the series of smaller holes includes at least 20 holes.

13. A pellet-shaped article conveying apparatus comprising:
    a conveyer mechanism to convey a plurality of pellet-shaped articles along a selected path, said conveyer including a plurality of receiving products each adapted to receive one of the pellet-shaped articles; and
    the laser drilling system of claim 1.

14. The pellet-shaped article conveying apparatus of claim 13, wherein the controller controls the laser and the conveyer mechanism.

15. The pellet-shaped article conveying apparatus of claim 13, wherein the laser includes a galvo with two mirrors mounted to respective servo motors, wherein the controller is set to control pointing of the laser towards the conveyer mechanism by adjusting the mirror positions via the respective servo.

16. The pellet-shaped article conveying apparatus of claim 15, wherein the galvo is electronically geared to the conveyer mechanism.

17. An apparatus for conveying pellet-shaped articles comprising:
    a conveyer to transport a plurality of articles, said conveyer having a plurality of axially spaced rows of pockets each structured to receive one of the articles; and
    a laser system comprising:
        a laser to create a laser beam;
        a deflector to deflect the laser beam; and
        a controller to allow the deflector to split the laser beam into a plurality of beams that are directed to the articles in the axially spaced rows of the conveyer, wherein the controller is set to control the deflector such that the laser beam impacts each article within its respective pocket to define a predetermined pattern defined by a series of holes having a predetermined depth.

18. The apparatus according to claim 17, wherein the laser beam depth is controlled in the range of 450-500 µm.

19. The apparatus according to claim 18, wherein the depth of the pattern is equal to or greater than a thickness of a coating on the articles.

20. The apparatus according to claim 18, wherein the laser beam depth is controlled by pulsing the laser beam one or more times.

21. The apparatus according to claim 18, wherein the controller is set to control the laser to laser each article for about 30-300 ms with a pulse period of about 400-600 ms and a pulse width of about 40-60 ms.

22. The apparatus according to claim 21, wherein the laser is controllable to laser each article for about 100-200 ms.

23. The apparatus according to claim 22, wherein the laser is controllable to laser each article for about 150 ms.

24. The apparatus according to claim 17, wherein the laser beam is configured to drill a hole having a diameter in the range of 50 µm to about 6 mm.

25. The apparatus according to claim 24, wherein for holes in the range of 1 mm to 6 mm, a series of smaller holes are combined to form said drilled hole.

26. The apparatus according to claim 17, wherein the series of holes includes at least 5 holes.

27. The apparatus according to claim 26, wherein the series of holes includes at least 10 holes.

28. The apparatus according to claim 27, wherein the series of holes includes at least 20 holes.

29. An apparatus for conveying pellet-shaped articles, comprising:
    a conveyer mechanism having a conveyer belt with a plurality of carrier bars each having at least one row of article receiving pockets;
    a laser unit to create a laser beam;
    a galvometer having at least one movable mirror mounted to a servo;
    a multi-axis controller to control the conveyer belt, the position of the mirror and the laser unit, such that the mirror position can be adjusted to sequentially direct the laser beam to generate a pattern on each of the articles in the at least one row of receiving pockets.

30. The apparatus of claim 29, wherein the pattern includes a series of small holes having a predetermined depth.

31. The apparatus according to claim 30, wherein the laser beam depth is controlled in the range of 450-500 µm.

32. The apparatus according to claim 31, wherein the depth of the pattern is equal to or greater than a thickness of a coating on the articles.

33. The apparatus according to claim 29, wherein the laser unit is set to laser each article for about 30-300 ms with a pulse period of about 400-600 ms and a pulse width of about 40-60 ms.

34. The apparatus according to claim 33, wherein the laser unit is controllable to laser each article for about 100-200 ms.

35. The apparatus according to claim 34, wherein the laser unit is controllable to laser each article for about 150 ms.

36. The apparatus according to claim 29, wherein the series of holes includes at least 5 holes.

37. The apparatus according to claim 36, wherein the series of holes includes at least 10 holes.

38. The apparatus according to claim 37, wherein the series of holes includes at least 20 holes.

39. The apparatus according to claim 29, wherein the controller is set to control the galvometer and mirror position based on encoder feedback of the conveyer belt position and speed.

* * * * *